US011771434B2

(12) United States Patent
Bellomo et al.

(10) Patent No.: US 11,771,434 B2
(45) Date of Patent: Oct. 3, 2023

(54) ARTERY MEDICAL APPARATUS AND METHODS OF USE THEREOF

(71) Applicant: Restore Medical Ltd., Or Yehuda (IL)

(72) Inventors: Stephen F. Bellomo, Zichron Yakov (IL); Ben Adam Friesem, Tel Aviv (IL)

(73) Assignee: Restore Medical Ltd., Or Yehuda (IL)

( * ) Notice: Subject to any disclaimer, the term of this patent is extended or adjusted under 35 U.S.C. 154(b) by 269 days.

(21) Appl. No.: 15/716,667

(22) Filed: Sep. 27, 2017

(65) Prior Publication Data

US 2018/0085128 A1 Mar. 29, 2018

Related U.S. Application Data

(60) Provisional application No. 62/400,695, filed on Sep. 28, 2016.

(51) Int. Cl.
*A61B 17/12* (2006.01)
*A61F 2/90* (2013.01)
*A61F 2/06* (2013.01)
*A61B 5/00* (2006.01)
*A61B 17/00* (2006.01)

(52) U.S. Cl.
CPC .. *A61B 17/12036* (2013.01); *A61B 17/12109* (2013.01); *A61B 17/12168* (2013.01); *A61B 17/12172* (2013.01); *A61F 2/90* (2013.01); *A61B 5/4848* (2013.01); *A61B 17/1215* (2013.01); *A61B 2017/00526* (2013.01); *A61F 2/06* (2013.01); *A61F 2002/068* (2013.01)

(58) Field of Classification Search
CPC ........ A61B 17/12036; A61B 17/12172; A61B 17/12109; A61B 2017/00526; A61B 5/4848; A61B 17/12168; A61B 17/1215; A61B 2017/12004; A61B 17/12; A61F 2/06; A61F 2002/068; A61F 2/90
See application file for complete search history.

(56) References Cited

U.S. PATENT DOCUMENTS

| | | | |
|---|---|---|---|
| 3,730,186 | A | 5/1973 | Edmunds, Jr. et al. |
| 4,183,102 | A | 1/1980 | Guiset |
| 4,425,908 | A | 1/1984 | Simon |
| 4,601,718 | A | 7/1986 | Possis et al. |

(Continued)

FOREIGN PATENT DOCUMENTS

| | | |
|---|---|---|
| CN | 1430490 | 7/2003 |
| CN | 1672644 | 9/2005 |

(Continued)

OTHER PUBLICATIONS

Translation of EP 1 870 057 A1: http://translationportal.epo.org/emtp/translate/?ACTION=description-retrieval&COUNTRY=FR&ENGINE=google&FORMAT=docdb&KIND=A1&LOCALE=en_EP&NUMBER=2902642&OPS=ops.epo.org/3.2&SRCLANG=fr&TRGLANG=en.*

(Continued)

*Primary Examiner* — Tuan V Nguyen

(57) ABSTRACT

Methods and medical apparatus for deployment within an anatomical blood vessel. The medical apparatuses comprising: a first tubular wall, a second tubular wall, within the first tubular wall, and a constricting element configured to constrict a circumference of a portion of the second tubular wall; the combination of the first tubular wall, the second tubular wall and the constricting element forms a diametrical reducer.

41 Claims, 9 Drawing Sheets

(56) References Cited

U.S. PATENT DOCUMENTS

| | | |
|---|---|---|
| 4,950,276 A | 8/1990 | Vince |
| 5,156,620 A | 10/1992 | Pigott |
| 5,167,628 A | 12/1992 | Boyles |
| 5,330,528 A | 7/1994 | Lazim |
| 5,332,403 A | 7/1994 | Kolff |
| 5,383,892 A | 1/1995 | Cardon et al. |
| 5,423,851 A | 6/1995 | Samuels |
| 5,554,180 A | 9/1996 | Turk |
| 5,554,185 A | 9/1996 | Block et al. |
| 5,618,301 A | 4/1997 | Hauenstein et al. |
| 5,662,711 A | 9/1997 | Douglas |
| 5,683,411 A | 11/1997 | Kavteladze et al. |
| 5,755,779 A | 5/1998 | Horiguchi |
| 6,120,534 A * | 9/2000 | Ruiz ................ A61F 2/86 623/1.3 |
| 6,312,462 B1 | 11/2001 | McDermott et al. |
| 6,471,635 B1 | 10/2002 | Forsell |
| 6,533,800 B1 | 3/2003 | Barbut |
| 6,562,066 B1 | 5/2003 | Martin |
| 6,595,980 B1 | 7/2003 | Barbut |
| 6,616,624 B1 | 9/2003 | Kieval |
| 6,638,257 B2 | 10/2003 | Amplatz |
| 6,790,230 B2 | 9/2004 | Beyersdorf et al. |
| 6,936,057 B1 | 8/2005 | Nobles |
| 6,953,476 B1 | 10/2005 | Shalev |
| 7,001,409 B2 | 2/2006 | Amplatz |
| 7,128,750 B1 | 10/2006 | Stergiopulos |
| 7,158,832 B2 | 1/2007 | Kieval et al. |
| 7,201,772 B2 | 4/2007 | Schwammenthal et al. |
| 7,331,993 B2 | 9/2008 | White et al. |
| 7,442,204 B2 | 10/2008 | Schwammenthal et al. |
| 7,497,873 B1 | 3/2009 | Bruckheimer |
| 7,670,367 B1 | 2/2010 | Chouinard et al. |
| 7,862,502 B2 | 1/2011 | Pool et al. |
| 7,935,144 B2 | 5/2011 | Robin et al. |
| 7,983,765 B1 | 7/2011 | Doan et al. |
| 7,998,220 B2 | 8/2011 | Murphy |
| 8,070,708 B2 | 12/2011 | Rottenberg et al. |
| 8,091,556 B2 | 1/2012 | Keren et al. |
| 8,556,954 B2 | 10/2013 | Ben MuVhar et al. |
| 8,597,349 B2 | 12/2013 | Alkhatib |
| 8,663,314 B2 | 3/2014 | Wood et al. |
| 8,696,611 B2 | 4/2014 | Nitzan et al. |
| 8,764,772 B2 | 7/2014 | Tekulve |
| 8,808,356 B2 | 8/2014 | Braido et al. |
| 8,858,612 B2 | 10/2014 | Ben-Muvhar et al. |
| 8,911,489 B2 | 12/2014 | Ben-Muvhar |
| 8,940,040 B2 | 1/2015 | Shariari |
| 9,034,034 B2 | 5/2015 | Nitzan et al. |
| 9,125,567 B2 | 9/2015 | Gross et al. |
| 9,393,384 B1 | 7/2016 | Kapur et al. |
| 9,474,839 B2 | 10/2016 | Oran |
| 9,532,868 B2 | 1/2017 | Braido |
| 9,572,661 B2 | 2/2017 | Robin et al. |
| 9,603,708 B2 | 3/2017 | Robin et al. |
| 9,629,715 B2 | 4/2017 | Nitzan et al. |
| 9,649,480 B2 | 5/2017 | Sugimoto et al. |
| 9,668,861 B2 | 6/2017 | McGuckin, Jr. |
| 9,681,948 B2 | 6/2017 | Levi et al. |
| 9,681,949 B2 | 6/2017 | Braido et al. |
| 9,687,242 B2 | 6/2017 | Hendriksen et al. |
| 9,707,382 B2 | 7/2017 | Nitzan et al. |
| 9,713,696 B2 | 7/2017 | Yacoby et al. |
| 9,724,499 B2 | 8/2017 | Rottenberg et al. |
| 9,744,059 B2 | 8/2017 | Ben-Muvhar |
| 9,775,636 B2 | 10/2017 | Fazio et al. |
| 9,849,006 B2 | 12/2017 | Ak et al. |
| 10,010,328 B2 | 7/2018 | Cragg et al. |
| 10,022,128 B2 | 7/2018 | Bödewadt et al. |
| 10,492,933 B2 | 12/2019 | Jenni |
| 10,568,634 B2 | 2/2020 | Goldie et al. |
| 10,667,931 B2 | 6/2020 | Bruckheimer et al. |
| 10,835,394 B2 | 11/2020 | Nae et al. |
| 10,912,645 B2 | 2/2021 | Rottenberg et al. |
| 11,135,054 B2 | 10/2021 | Nitzan et al. |
| 11,224,503 B2 | 1/2022 | Karavany et al. |
| 11,253,685 B2 | 2/2022 | Fahey et al. |
| 11,357,610 B2 | 6/2022 | Karavany et al. |
| 11,364,132 B2 | 6/2022 | Bellomo et al. |
| 2001/0053330 A1 | 12/2001 | Ozaki |
| 2002/0107536 A1 | 8/2002 | Hussein |
| 2003/0032976 A1 | 2/2003 | Boucek |
| 2003/0097172 A1 | 5/2003 | Shalev et al. |
| 2003/0144575 A1 | 7/2003 | Forsell |
| 2003/0149473 A1 | 8/2003 | Chouinard et al. |
| 2003/0167068 A1 | 9/2003 | Amplatz |
| 2003/0236568 A1 | 12/2003 | Hojeibane et al. |
| 2004/0077988 A1 | 4/2004 | Tweden et al. |
| 2004/0111006 A1 | 6/2004 | Alfemess et al. |
| 2004/0236412 A1 | 11/2004 | Brar et al. |
| 2005/0055082 A1* | 3/2005 | Ben Muvhar .... A61B 17/12172 623/1.15 |
| 2005/0096734 A1 | 5/2005 | Majercak et al. |
| 2005/0148925 A1 | 7/2005 | Rottenberg et al. |
| 2005/0165344 A1 | 7/2005 | Dobak, III |
| 2005/0171556 A1 | 8/2005 | Murphy |
| 2005/0182483 A1 | 8/2005 | Osborne et al. |
| 2005/0234388 A1 | 10/2005 | Amos et al. |
| 2005/0273160 A1 | 12/2005 | Lashinski et al. |
| 2005/0283962 A1 | 12/2005 | Boudjemline |
| 2006/0009800 A1 | 1/2006 | Christianson et al. |
| 2006/0025855 A1 | 2/2006 | Lashinski et al. |
| 2006/0030920 A1 | 2/2006 | Ben-Muvhar |
| 2006/0106449 A1 | 5/2006 | Ben Muvhar |
| 2006/0106450 A1 | 5/2006 | Ben Muvhar |
| 2006/0122692 A1 | 6/2006 | Gilad et al. |
| 2006/0149360 A1 | 7/2006 | Schwammenthal et al. |
| 2006/0178740 A1 | 8/2006 | Stacchino et al. |
| 2006/0241745 A1 | 10/2006 | Solem |
| 2007/0038259 A1 | 2/2007 | Kieval et al. |
| 2007/0043435 A1 | 2/2007 | Seguin et al. |
| 2007/0179590 A1 | 8/2007 | Lu et al. |
| 2007/0198097 A1 | 8/2007 | Zegdi |
| 2007/0213813 A1 | 9/2007 | Von Segesser et al. |
| 2008/0027268 A1 | 1/2008 | Buckner et al. |
| 2008/0097497 A1 | 4/2008 | Assad et al. |
| 2008/0140110 A1 | 6/2008 | Spence |
| 2008/0194905 A1 | 8/2008 | Walsh |
| 2008/0208329 A1 | 8/2008 | Bishop et al. |
| 2009/0099653 A1 | 4/2009 | Suri et al. |
| 2009/0112312 A1 | 4/2009 | LaRose et al. |
| 2009/0149950 A1 | 6/2009 | Wampler |
| 2009/0198315 A1 | 8/2009 | Boudjemline |
| 2009/0270974 A1 | 10/2009 | Berez |
| 2010/0023046 A1* | 1/2010 | Heidner ............ A61B 17/12109 606/191 |
| 2010/0057192 A1 | 3/2010 | Celermajer |
| 2010/0125288 A1 | 5/2010 | Gelfand |
| 2010/0185277 A1 | 7/2010 | Braido et al. |
| 2010/0222633 A1 | 9/2010 | Poirier |
| 2010/0249911 A1 | 9/2010 | Alkhatib |
| 2010/0286758 A1 | 11/2010 | Berglund |
| 2011/0021864 A1 | 1/2011 | Criscione et al. |
| 2011/0046710 A1 | 2/2011 | Mangiardi et al. |
| 2011/0054589 A1 | 3/2011 | Bashiri et al. |
| 2011/0071624 A1 | 3/2011 | Finch et al. |
| 2011/0098800 A1 | 4/2011 | Braido et al. |
| 2011/0098802 A1 | 4/2011 | Braido et al. |
| 2011/0213408 A1 | 9/2011 | Gross et al. |
| 2011/0306916 A1 | 12/2011 | Nitzan et al. |
| 2012/0101572 A1 | 4/2012 | Kovalsky et al. |
| 2012/0123195 A1 | 5/2012 | Woodruff et al. |
| 2012/0123556 A1 | 5/2012 | Durgin |
| 2012/0149978 A1 | 6/2012 | Olivera et al. |
| 2012/0165928 A1 | 6/2012 | Nitzan et al. |
| 2012/0310323 A1* | 12/2012 | Roeder ................ A61F 2/966 623/1.12 |
| 2013/0073026 A1 | 3/2013 | Russo et al. |
| 2013/0096580 A1 | 4/2013 | Cohn et al. |
| 2013/0103162 A1 | 4/2013 | Costello |
| 2013/0172981 A1 | 7/2013 | Gross et al. |
| 2013/0178750 A1 | 7/2013 | Sheehan et al. |
| 2013/0261531 A1* | 10/2013 | Gallagher ........ A61M 5/16813 604/9 |

(56) References Cited

U.S. PATENT DOCUMENTS

| | | |
|---|---|---|
| 2013/0274648 A1 | 10/2013 | Weinberger |
| 2014/0012181 A1 | 1/2014 | Sugimoto et al. |
| 2014/0039537 A1 | 2/2014 | Carrison |
| 2014/0128957 A1 | 5/2014 | Losordo et al. |
| 2014/0155997 A1 | 6/2014 | Braido |
| 2014/0277425 A1 | 9/2014 | Dakin |
| 2014/0303710 A1 | 10/2014 | Zhang et al. |
| 2014/0324094 A1 | 10/2014 | Weber et al. |
| 2014/0350565 A1 | 11/2014 | Yacoby et al. |
| 2014/0350668 A1 | 11/2014 | Delaloye et al. |
| 2014/0364686 A1 | 12/2014 | McClurg |
| 2015/0073544 A1 | 3/2015 | Gorman, III et al. |
| 2015/0148896 A1 | 5/2015 | Karapetian et al. |
| 2015/0174308 A1 | 6/2015 | Oran et al. |
| 2016/0151153 A1 | 6/2016 | Sandstrom et al. |
| 2016/0296317 A1 | 10/2016 | Timmermans et al. |
| 2017/0042551 A1 | 2/2017 | Celermajer et al. |
| 2017/0065402 A1 | 3/2017 | Tozzi et al. |
| 2017/0113026 A1 | 4/2017 | Finch |
| 2017/0172771 A1 | 6/2017 | Bruckjeimer et al. |
| 2017/0215885 A1 | 8/2017 | Goldie et al. |
| 2017/0216025 A1 | 8/2017 | Nitzan et al. |
| 2017/0325946 A1 | 11/2017 | Bell et al. |
| 2017/0340441 A1 | 11/2017 | Rowe |
| 2017/0340460 A1 | 11/2017 | Rosen et al. |
| 2017/0367855 A1 | 12/2017 | Jenni |
| 2018/0021156 A1 | 1/2018 | Ben-Muvhar et al. |
| 2018/0036109 A1 | 2/2018 | Karavany et al. |
| 2018/0085128 A1 | 3/2018 | Belllomo et al. |
| 2018/0092732 A1 | 4/2018 | Kringle et al. |
| 2019/0000483 A1 | 1/2019 | Mogensen |
| 2019/0307459 A1 | 10/2019 | Celermajer et al. |
| 2020/0000582 A1 | 1/2020 | Lashinski et al. |
| 2020/0205962 A1 | 7/2020 | Karavant et al. |
| 2020/0229956 A1 | 7/2020 | Jackson et al. |
| 2020/0289299 A1 | 9/2020 | Bruckheimer et al. |
| 2020/0297516 A1 | 9/2020 | Bellomo et al. |
| 2020/0352696 A1 | 11/2020 | Radhakrishnan et al. |
| 2020/0360024 A1 | 11/2020 | Bellomo et al. |
| 2021/0161643 A1 | 6/2021 | Totten et al. |
| 2021/0169634 A1 | 6/2021 | Karavany et al. |
| 2021/0290358 A1 | 9/2021 | Goodman et al. |
| 2021/0338465 A1 | 11/2021 | Bruckheimer et al. |
| 2022/0015889 A1 | 1/2022 | Lima et al. |
| 2022/0022881 A1 | 1/2022 | Celermajer et al. |
| 2022/0039938 A1 | 2/2022 | Karavany et al. |
| 2022/0117765 A1 | 4/2022 | Yacoby et al. |
| 2022/0241063 A1 | 8/2022 | Karavany et al. |

FOREIGN PATENT DOCUMENTS

| | | | |
|---|---|---|---|
| CN | 101687088 | | 3/2010 |
| CN | 102764170 | | 11/2012 |
| CN | 102961200 | | 3/2013 |
| CN | 103202735 | | 7/2013 |
| CN | 103930042 | | 7/2014 |
| CN | 204106100 | | 1/2015 |
| CN | 105392431 | | 3/2016 |
| DE | 10102045 | | 1/2003 |
| EP | 1576929 | | 9/2005 |
| EP | 1849440 | A1 | 10/2007 |
| EP | 1870057 | | 12/2007 |
| EP | 1870057 | A1 | 12/2007 |
| EP | 2567663 | | 3/2013 |
| EP | 3300672 | | 4/2018 |
| WO | WO 2001/035861 | | 5/2001 |
| WO | WO 2001/035861 | A1 | 5/2001 |
| WO | WO 03/028522 | | 4/2003 |
| WO | WO 2003/028522 | A2 | 4/2003 |
| WO | WO 2005/084730 | | 9/2005 |
| WO | WO 2006/131930 | | 12/2006 |
| WO | WO 2007/129220 | A2 | 11/2007 |
| WO | WO 2007/144782 | A2 | 12/2007 |
| WO | WO 2011/156176 | | 12/2011 |
| WO | WO 2013/096548 | | 6/2013 |
| WO | WO 2016/013006 | | 1/2016 |
| WO | WO 2016/096529 | | 6/2016 |
| WO | WO 2016/096529 | A1 | 6/2016 |
| WO | WO-2016096529 | A1 * | 6/2016 ....... A61B 17/12036 |
| WO | WO 2017/024357 | | 2/2017 |
| WO | WO 2017/194437 | | 11/2017 |
| WO | WO 2018/225059 | | 12/2018 |
| WO | WO 2020/023512 | | 1/2020 |
| WO | WO 2020/109979 | | 6/2020 |
| WO | WO 2023/281507 | | 1/2023 |

OTHER PUBLICATIONS

Ahmadi et ai. "Percutaneously adjustable pulmonary artery band" The Annals of thoracic surgery. Dec. 1, 1995;60:S520-2.

Amahzoune et al. "A new endovascular size reducer for large pulmonary outflow tract" European Journal of Cardio-Thoracic Surgery. Mar. 1, 2010;37(3):730-2.

Basquin et al. "Transcatheter valve insertion in a model of enlarged right ventricular outflow tracts" The Journal of thoracic and cardiovascular surgery. Jan. 31, 2010;139(1):198-208.

Boudjemline et al. "Percutaneous pulmonary valve replacement in a large right ventricular outflow tract" Journal of the American College of Cardiology. Mar. 17, 2004;43(6):1082-7.

Boudjemline et al. "Steps toward the percutaneous replacement of atrioventricular valves: an experimental study" Journal of the American College of Cardiology. Jul. 19, 2005;46(2):360-5.

Corno et al. "The non-circular shape of FloWatch@-PAB prevents the need for pulmonary artery reconstruction after banding: computational fluid dynamics and clinical correlations" Eurobean journal of cardio-thoracic surgery. Jan. 1, 2006:29(1):93-9.

Dibardino et al. A method of transcutaneously adjustable pulmonary artery banding for staged left ventricular retraining. The Journal of thoracic and cardiovascular surgery. Sep. 30, 2012;144(3):553-6.

European Search Report for European Application No. 17193799.8 dated Jan. 19, 2018.

Horita et al. "Development of a reexpandable covered stent for children" Catheterization and cardiovascular interventions. Nov. 1, 2006;68(5):727-34.

Le Bret et al. "A new percutaneously adjustable, thoracoscopically implantable, pulmonary artery banding: an experimental study" The Annals of thoracic surgery. Oct. 31, 2001;72(4):1358-61.

Mollet et al. "Development of a device for transcatheter pulmonary artery banding: evaluation in animals" European heart journal. Oct. 31, 2006;27(24):3065-72.

Mollet et al. "Off-pump replacement of the pulmonary valve in large right ventricular outflow tracts: a transcatheter approach using an intravascular infundibulum reducer" Pediatric research. Oct. 1, 2007;62(4):428-33.

Nakahata et al. "Percutaneous bilateral pulmonary artery bandingusing re-expandable covered stent: preliminary animal study" Kitasato Med J. Sep. 2011;41:165-9.

Schranz et al. "Pulmonary artery banding in infants and young children with left ventricular dilated cardiomyopathy: a novel therapeutic strategy before heart transplantation" The Journal of Heart and Lung Transplantation. May 31, 2013;32(5):475-81.

Talwar et al. "Changing outcomes of pulmonary artery banding with the percutaneously adjustable pulmonary artery band" The Annals of thoracic surgery. Feb. 29, 2008;85(2):593-8.

Watanabe et al. "How to clamp the main pulmonary artery during video-assisted thoracoscopic surgery lobectomy" European journal of cardio-thoracic surgery. Jan. 1, 2007;31(1):129-31.

European Search Report and the European Search Opinion dated Jan. 19, 2018 From the European Patent Office Re. Application No. 17193799.8. (9 Pages).

Office Action dated Oct. 19, 2020 From the Israel Patent Office Re. Application No. 254791 and Its Translation Into English. (6 Pages).

Notification of Office Action and Search Report dated Nov. 30, 2021 From the State Intellectual Property Office of the People's Republic of China Re. Application No. 201710896715.3 and Its Summary in English.

Final Official Action dated Dec. 21, 2021 from US Patent and Trademark Office Re. U.S. Appl. No. 16/616,465. (6 pages).

(56) References Cited

OTHER PUBLICATIONS

International Preliminary Report on Patentability dated Dec. 19, 2019 From the International Bureau of WIPO Re. Application No. PCT/IL2018/050604. (9 Pages).
International Preliminary Report on Patentability dated Jan. 24, 2017 From the International Bureau of WIPO Re. Application No. PCT/IL2015/050745. (8 Pages).
International Search Report and the Written Opinion dated Nov. 5, 2015 From the International Searching Authority Re. Application No. PCT/IL2015/050745. (14 Pages).
International Search Report and the Written Opinion dated Sep. 20, 2018 From the International Searching Authority Re. Application No. PCT/IL2018/050604. (12 Pages).
Notice of Allowance Dated Jan. 24, 2020 From the U.S. Patent and Trademark Office Re. U.S. Appl. No. 15/327,075. (8 pages).
Office Action dated Jun. 7, 2021 From the Israel Patent Office Re. Application No. 250181 and Its Translation Into English. (7 Pages).
Office Action dated May 12, 2020 From the Israel Patent Office Re. Application No. 250181 and Its Translation Into English. (7 Pages).
Official Action dated Feb. 2, 2018 From the U.S. Patent and Trademark Office Re. U.S. Appl. No. 15/327,075. (15 pages).
Official Action dated Jun. 5, 2019 From the U.S. Patent and Trademark Office Re. U.S. Appl. No. 15/327,075. (6 Pages).
Official Action dated Sep. 6, 2018 From the U.S. Patent and Trademark Office Re. U.S. Appl. No. 15/327,075. (9 pages).
Official Action dated Jul. 14, 2021 from the U.S. Patent and Trademark Office Re. U.S. Appl. No. 16/616,465. (16 pages).
Official Action dated Dec. 20, 2018 From the U.S. Patent and Trademark Office Re. U.S. Appl. No. 15/327,075. (12 pages).
Official Action dated Sep. 27, 2019 From the U.S. Patent and Trademark Office Re. U.S. Appl. No. 15/327,075. (6 Pages).
Restriction Official Action dated Apr. 30, 2021 From the U.S. Patent and Trademark Office Re. U.S. Appl. No. 16/616,465, (7 Pages).
Supplementary European Search Report and the European Search Opinion dated Feb. 4, 2021 From the European Patent Office Re. Application No. 18812772.4. (7 Pages).
Supplementary European Search Report and the European Search Opinion dated Feb. 9, 2018 From the European Patent Office Re. Application No. 15825239.5. (7 Pages).
Bailey "Back to the Future! Bold New Indication for Pulmonary Artery Banding", The Journal of Heart and Lung Transplantation, 32(5): 482-483, May 1, 2013.
Schranz et al. "Pulmonary Artery Banding in Infants and Young Children With Lleft Ventricular Dilated Cardiomyopathy: A Novel Therapeutic Strategy Before Heart Transplantation", The Journal of Heart and Lung Transplantation, 32(5):475-481, May 31, 2013.
English Summary dated Mar. 17, 2022 of Notification of Office Action and Search Report dated Mar. 9, 2022 From the State Intellectual Property Office of the People's Republic of China Re. Application No. 201880036104.4. (2 Pages).
Notice of Allowance dated Mar. 18, 2022 from U.S. Patent and Trademark Office Re. U.S. Appl. No. 16/616,465. (22 pages).
Notification of Office Action and Search Report dated Mar. 9, 2022 From the State Intellectual Property Office of the People's Republic of China Re. Application No. 201880036104.4. (8 Pages).
Official Action dated Aug. 16, 2022 from U.S. Patent and Trademark Office Re. U.S. Appl. No. 16/888,872. (43 pages).
Notification of Office Action and dated Jul. 5, 2022 From the State Intellectual Property Office of the People's Republic of China Re. Application No. 201710896715.3 and Its Summary in English. (5 Pages).
Office Action dated Jul. 13, 2022 From the Israel Patent Office Re. Application No. 250181. (5 Pages).
Translation dated Jul. 20, 2022 of Office Action dated Jul. 13, 2022 From the Israel Patent Office Re. Application No. 250181. (4 Pages).
Official Action Dated Apr. 5, 2023 from the U.S. Patent and Trademark Office Re. U.S. Appl. No. 16/984,166. (25 pages).
Official Action dated Oct. 18, 2022 from the U.S. Patent and Trademark Office Re. U.S. Appl. No. 16/984,166. (55 pages).
Office Action dated Oct. 30, 2022 From the Israel Patent Office Re. Application No. 271184. (4 Pages).
International Search Report and the Written Opinion dated Oct. 12, 2022 From the International Searching Authority Re. Application No. PCT/IL2022/050724. (15 Pages).
Santamore et al. "Ventricular Interdependence: Significant Left Ventricular Contributions to Right Ventricular Systolic Function", Progress in Cardiovascular Diseases, 40(4): 289-308, Jan./Feb. 1998.
Communication Pursuant to Article 94(3) EPC dated May 24, 2023 From the European Patent Office Re. Application No. 17193799.8. (4 Pages).
Notice of Allowance dated Mar. 22, 2023 from the U.S. Patent and Trademark Office Re. Application No. 16/888.872. (16 pages).

* cited by examiner

Distal Side                    Proximal Side

ARTERY MEDICAL APPARATUS AND METHODS OF USE THEREOF

CROSS REFERENCE TO RELATED APPLICATIONS

This application claims the benefit of U.S. Provisional Patent Application No. 62/400,695 filed on Sep. 28, 2016, which is incorporated herein by reference in its entirety.

FIELD OF INTEREST

The current invention relates to a medical device to be positioned within the main pulmonary artery and/or the pulmonary artery branches, and to methods of use thereof for treating, reducing the severity of, or reducing symptoms associated with, or any combination thereof, congestive heart failure, including left ventricular failure, wherein use may in certain embodiments, affect the position and function of the interventricular septum during systole.

BACKGROUND OF THE INVENTION

Congestive heart failure (CHF) means the heart does not pump out sufficient blood to meet the body's demands CHF can result from either a reduced ability of the heart muscle to contract (systolic failure) or from a mechanical problem that limits the ability of the heart's chambers to fill with blood (diastolic failure). When weakened, the heart is unable to keep up with the demands placed upon it and the left ventricle (LV) gets backed up or congested. CHF is a progressive disease. Failure of the left side of the heart (left-heart failure/left-sided failure/left-ventricle failure) is the most common form of the disease.

CHF affects people of all ages including children, but it occurs most frequently in those over age 60, and is the leading cause of hospitalization and death in that age group. Current treatments of CHF include lifestyle changes, medications, and surgery to bypass blocked blood vessels, replace regurgitant or stenotic valves, install stents to open narrowed coronary vessels, install pump assist devices or transplantation of the heart.

Normal cardiac contraction is a finely tuned orchestrated activity dependent on muscle function, ventricular geometry and loading conditions termed preload and afterload. When CHF due to LV systolic failure occurs, it is typically associated with changes in the geometry of the ventricles, often called remodeling. The LV becomes dilated and the interventricular septum is deflected into the right ventricle (RV), resulting in decreased LV output/pumping efficiency. The efficient systolic function of the LV is dependent not only on the strength of the myocardium but also on the LV geometry, the position and shape of the interventricular septum and the geometry and function of the RV. Interventricular dependence has been documented in experimental studies which have evaluated both normal and pathological preparations in animals. LV systolic function can be directly influenced by interventions affecting the RV and the position of the interventricular septum.

Surgical pulmonary artery banding (PAB) is a technique that was described more than 60 years ago and is still in use today for children and infants with congenital heart defects, such as overflow of blood to the lungs and volume overload of the RV. PAB is typically performed through a thoracotomy and involves wrapping a band around the exterior of the main pulmonary artery (MPA) and fixing the band in place, often with the use of sutures. Once applied, the band is tightened, narrowing the diameter of the MPA, increasing resistance to flow, reducing blood flow to the lungs, and reducing downstream pulmonary artery (PA) pressure.

Surgical PAB procedures involve the risks present with all surgical procedures. In addition, use of PAB has a number of particular disadvantages and drawbacks. Primary among these drawbacks is the inability of the surgeon performing the procedure to accurately assess, from the hemodynamic standpoint, the optimal final diameter to which the PA should be adjusted. Often, the surgeon must rely upon his or her experience in adjusting the band to achieve acceptable forward flow while decreasing the blood flow sufficiently to protect the pulmonary vasculature.

It is also not uncommon for the band to migrate towards one of the main pulmonary branches (usually the left), resulting in stenosis of the other main pulmonary branch (usually the right). There have also been reports of hardening of the vessels around the band due to buildup of calcium deposits and scarring of the PA wall beneath the band, which can also inhibit blood flow. Flow resistance due to PAB may change over time, and additional surgeries to adjust band tightness occur in up to one third of patients. The band is typically removed in a subsequent operation, for example, when a congenital malformation is corrected in the child or infant.

In addition to the classical use of PAB for treatment of congenital defects in infants and children, there has been a recent report of use of surgical PAB for left ventricle dilated cardiomyopathy (LVDCM) in infants and young children. This method includes increasing the pressure load on the right ventricle by placing a band around the pulmonary artery. The increased pressure in the right ventricle caused a leftward shift of the interventricular septum and improvement of left ventricle function. It was found that the optimal degree of constriction was achieved when the RV pressure was approximately 60% to 70% of the systemic level and so that the interventricular septum slightly moved to a midline position. The success of these procedures in infants and children has been reported to be possibly due to the potential for myocyte recovery and repopulation being significantly greater for infants and young children than for adults. However, it is the position of the inventors that the geometric improvements to the failing heart due to PAB may be responsible, at least partially, for the observed improvements in LV function, and therefore PAB for adult left ventricle heart failure may demonstrate similar improvement in LV function.

The MPA is not a favorable location for positioning an implant due to its relatively large diameter (~30 mm) and short length (~50 mm). The full length of the MPA is not usable for an implant due to the proximity to the pulmonary valve on one end, and the bifurcation to the pulmonary branches on the other. It is estimated that the usable length of the MPA for the implant is approximately 30 mm. Implantation of a short, wide device into the MPA is very difficult, and there is significant danger that the device will rotate or otherwise not be placed concentric with the MPA, in which case near complete blockage of the MPA could occur. In addition, the device may erroneously be placed either too close to the pulmonary valve or to the bifurcation.

It would be desirable to provide a relatively simple medical apparatus which could be implanted in a minimally-invasive fashion, and which would allow an adjustment of blood flow through a vessel. Gradual reduction in the diameter of the MPA may be desirable, but is not currently feasible with the surgical PAB approaches described above. In addition, it would be desirable to use the medical apparatus for treatment of the mature adult population suffering from left ventricle (LV) failure.

The methods and apparatuses of this invention describe a medical apparatus configured to reduce a diameter of a blood vessel for treating or at least reducing the severity of a congestive failure of the heart, such as but not limited to: systolic heart failure, diastolic heart failure, left ventricle (LV) heart failure, right ventricle (RV) heart failure, congenital defects of the heart for which surgical pulmonary artery banding (PAB) is used, and any other condition which requires pulmonary artery banding (PAB).

SUMMARY OF THE INVENTION

Some embodiments of the present invention provide a medical apparatus for deployment within an anatomical blood vessel comprising:
 a first tubular wall,
 a second tubular wall, within the first tubular wall, and
 a constricting element configured to constrict a circumference of a portion of the second tubular wall;
 the combination of the first tubular wall, the second tubular wall and the constricting element forms a diametrical reducer.

In some embodiments, the first tubular wall is connected at least at one end to the second tubular wall.

In some embodiments, at least a portion of the second tubular wall is coated with a coating material.

In some embodiments, the first and second tubular walls are concentric.

In some embodiments, material of the first and second tubular walls comprises at least one of the group consisting of: Nitinol, stainless steel, Titanium, Cobalt-Chromium alloy, Tantalum alloy, polymer, Platinum alloy and any combination thereof.

In some embodiments, the first tubular wall is made of a first material and the second tubular wall is made of a second material.

In some embodiments, the first and second tubular walls are manufactured by a process selected from: laser cutting, braiding, any combination thereof.

In some embodiments, the ratio between the medical apparatus's longitudinal length (L) and diameter of the first tubular wall (Dout) is smaller than 2.

In some embodiments, the constricting element comprises a loop section.

In some embodiments, the second tubular wall comprises at least one fixation element, configured to anchor the loop section and prevent it from longitudinal movement.

In some embodiments, the constriction element further comprises a tail section configured to be pulled and/or pushed to adjust the circumference of the loop section.

In some embodiments, the circumference of the loop section is locked at the adjusted circumference In some embodiments, the tail is configured to be detached after adjustment of the loop section circumference.

In some embodiments, the tail section is configured to extend out of the blood vessel and into a subcutaneous space.

In some embodiments, the constricting element is configured for circumference adjustment of the second tubular wall, while the medical apparatus is within the anatomic vessel.

In some embodiments, the constriction provides the second tubular wall with a radial neck section, configured for reduction of the effective diameter of the anatomical blood vessel.

In some embodiments, the medical apparatus is collapsible and configured to be delivered into the anatomic vessel via a catheter.

Some embodiments of the present invention provide a method for reduction of effective diameter of an anatomic vessel comprising:
 providing a medical apparatus having a second tubular wall deployed within a first tubular wall;
 deploying the medical apparatus within an anatomical blood vessel; and
 constricting at least a portion of the second tubular wall, thereby providing the second tubular wall with a radial neck section.

In some embodiments, the step of constricting is configured for forming a diametrical reducer for the anatomical blood vessel.

In some embodiments, the step of providing further comprises providing the medical apparatus with a constricting element configured for the constricting of the portion of the second tubular wall.

In some embodiments, the constricting element comprises a loop section and a tail section.

In some embodiments, the step of constricting further comprises adjusting the constriction, before, during, and/or after the step of the deploying.

In some embodiments, the step of the deploying comprises delivering the medical apparatus into the anatomical blood vessel via a catheter.

In some embodiments, the method further comprises a step of expanding the constricted portion of the second tubular wall, while within the anatomical blood vessel.

In some embodiments, the method further comprises a step of temporarily or permanently locking the constricted section of the second tabular wall to a specific circumference.

In some embodiments, the method further comprises a step of detaching the tail section from the constricting element.

In some embodiments, the method further comprises monitoring at least one physiological parameter.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may be understood by reference to the following detailed description when read with the accompanying drawings in which:

FIG. 6A illustrates a step of providing, FIG. 6B illustrates a step of delivering and FIG. 6C illustrates a step of adjusting of the constricting element;

Figure 1:
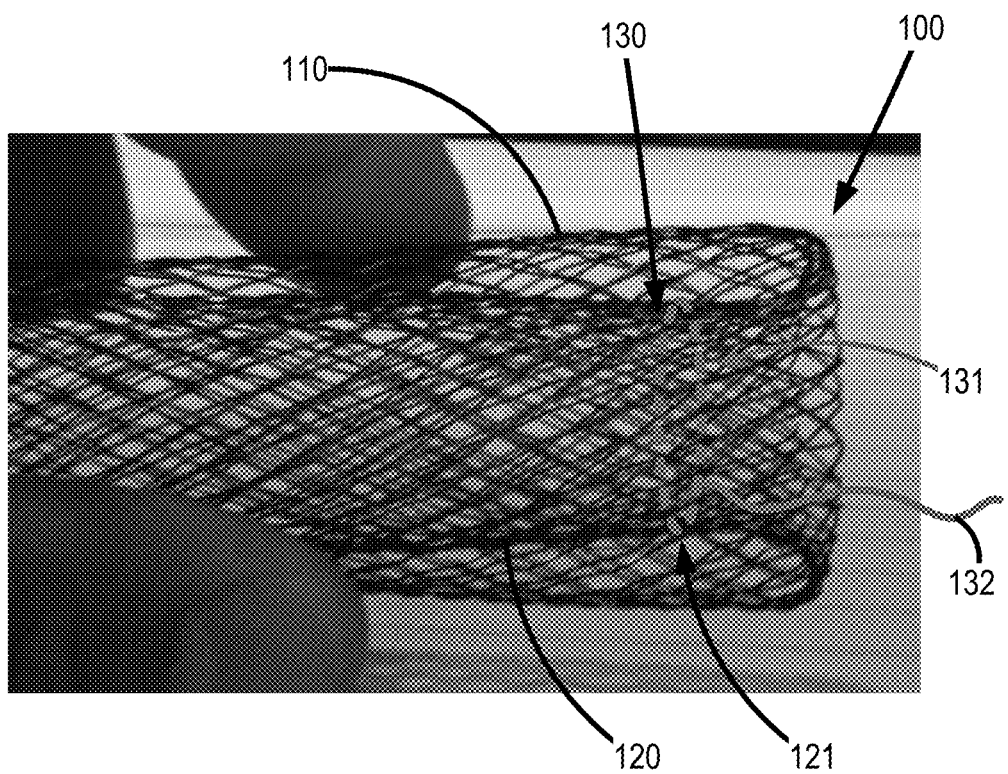
FIG. 1 conceptually depicts the medical apparatus, according to some embodiments of the invention, having an outer tubular wall, an inner tubular wall, and a constricting element.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

The following description is provided, alongside all chapters of the present invention, so that to enable any person skilled in the art to make use of the invention and sets forth the best modes contemplated by the inventor of carrying out this invention. Various modifications, however, will remain apparent to those skilled in the art, since the generic principles of the present invention have been defined specifically to provide a medical apparatus configured to reduce a diameter of a blood vessel for treating or at least reducing the severity of a congestive failure of the heart, such as but not limited to: systolic heart failure, diastolic heart failure, left ventricle (LV) heart failure, right ventricle (RV) heart failure, congenital defects of the heart for which surgical pulmonary artery banding (PAB) is used, and any other condition which requires pulmonary artery banding (PAB).

As used herein, in one embodiment, the term "about", refers to a deviance of between 0.0001-5% from the indicated number or range of numbers. In one embodiment, the term "about", refers to a deviance of between 1-10% from the indicated number or range of numbers. In one embodiment, the term "about", refers to a deviance of up to 25% from the indicated number or range of numbers.

According to some embodiments, the term "a" or "one" or "an" refers to at least one.

According to some embodiments the present invention provides a stent-like medical apparatus, as demonstrated at least in FIG. 1, which is configured to reduce the effective diameter of an anatomical blood vessel (150).

According to some embodiments, the medical apparatus (100) comprising:
 an outer tubular wall (110),
 an inner tubular wall (120) within the outer tubular wall, and
 a constricting element (130) configured to tighten at least a portion (121) of the inner tubular wall (120).

According to some embodiments, the combination of the outer tubular wall (110), the inner tubular wall (120) and the constricting element (130) forms a diametrical reducer, which is suitable to be implanted within an anatomical blood vessel (150).

According to some embodiments, the constriction (121) provides the inner tubular wall (120) with a radial neck section (125). According to some embodiments, the neck section (125) is configured for reduction of the effective diameter of an anatomical blood vessel (150). According to some embodiments a gradual adjustment of the constricting element (130) can cause a gradual reduction of the effective diameter of the anatomical blood vessel.

According to some embodiments, the inner and outer tubular walls (110,120) are connected at their proximal ends (as demonstrated at least in FIGS. 3, 10 and 11), at their distal ends (as demonstrated in FIGS. 5 and 12) or at both ends (not shown). According to a preferred embodiment, the inner and outer tubular walls (110,120) are connected at their proximal ends, configured for more stable blood flow within the medical apparatus (100).

According to some embodiments, in the case where the inner and outer tubular walls are connect at only one end (distal or proximal), the constriction or an adjustment of the constriction can cause a change in the overall longitudinal length ($L_{in}$) of the inner tubular wall (120).

According to some embodiments, the medical apparatus further comprises an arched section (140), for a non-limiting example a torus-like portion (as demonstrated at least in FIG. 2), configured to connect between the proximal ends and/or the distal ends of the inner and outer tubular walls (110,120).

According to some embodiments, the outer and inner tubular walls (110,120) are concentric. According to some embodiments, the medical apparatus is axisymmetric.

According to some embodiments, the material of the outer and inner tubular walls comprises at least one from the group consisting of: Nitinol, stainless steel, Titanium, Cobalt-Chromium alloy, Tantalum alloy, polymer, Platinum alloy and any combination thereof.

According to some embodiments, the outer tubular wall is made of a first material and the inner tubular wall is made of a second material. According to some embodiments, the outer and inner tubular walls are made of the same material.

Figure 5:
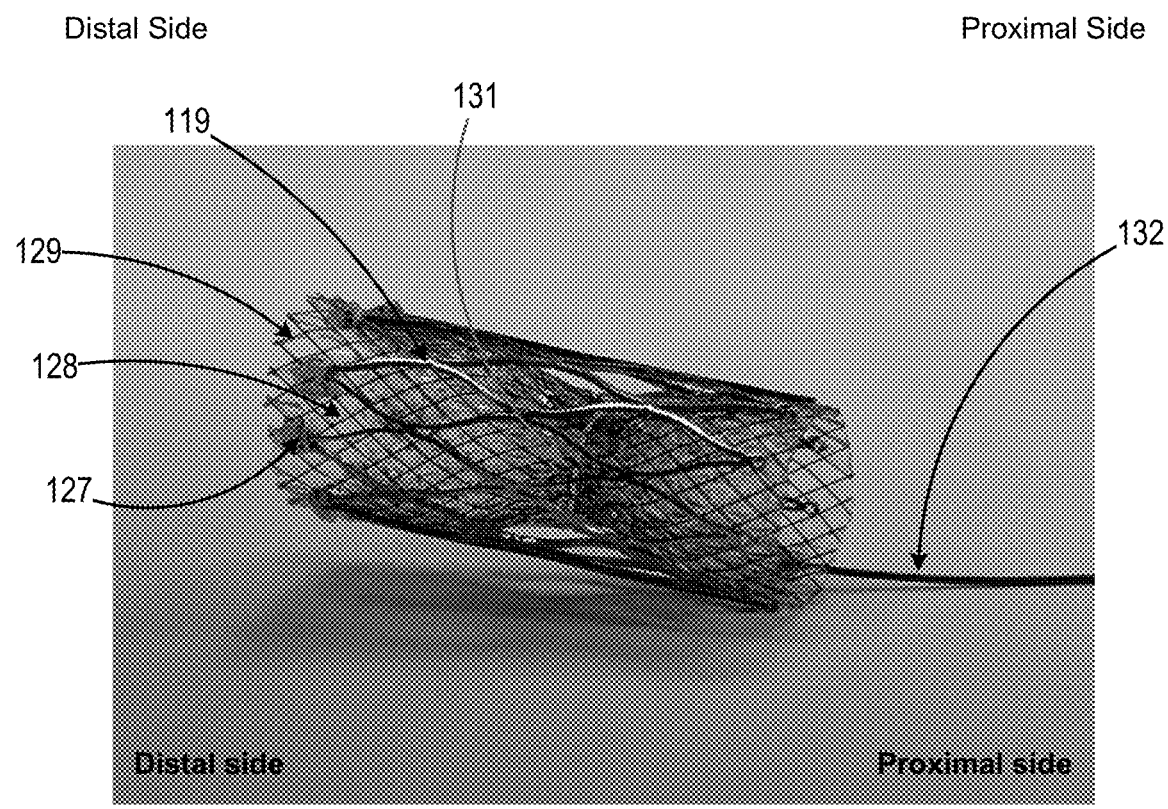
FIG. 5 conceptually depicts the medical apparatus, according to some embodiments of the invention, where the outer tubular wall is manufactured by laser cut process, and the inner tubular wall is manufactured by braiding process, the inner tubular wall is also demonstrated to have a coating material.

According to some embodiments, at least a part of the inner tubular wall is coated (128), as demonstrated in FIG. 5 in order to cause the blood flow in the blood vessel (150) to primarily flow through the inner tubular wall (120). The coating material can be selected, for a non-limiting example, from: silicone elastomers, urethane containing polymers (such as polyurethane, silicone-polyurethane, polycarbonate urethanes, and silicone polycarbonate urethanes), PTFB, PLA (including PLGA, PLLA), xenograft or allograft tissue (such as pericardial tissue).

According to some embodiments, at least one of the outer and inner tubular walls (110,120) is made of a collapsible memory shape material, therefore self-expanding material. According to some embodiments, at least one of the outer and inner tubular walls (110,120) is manufactured by laser cut process. According to some embodiments, at least one of the outer and inner tubular walls (110,120) is manufactured by braiding. According to a preferred embodiment the outer tubular wall (110) is manufactured by a laser cut process and the inner tubular wall (120) is manufactured by braiding (as shown in FIG. 5).

According to some embodiments, the ratio between the medical apparatus's (100) longitudinal length (L) and the diameter of the outer tubular wall (Dow) is smaller than a predetermined numeral ($N=L/D_{out}$) selected from the group consisting of: 3, 2.5, 2, 1.5, 1, 0.5, 0.3 and any ratio within this range. According to a preferred embodiment, N is smaller than 1.5. The dimension annotations for the medical apparatus can be found in FIG. 3.

Figure 3:
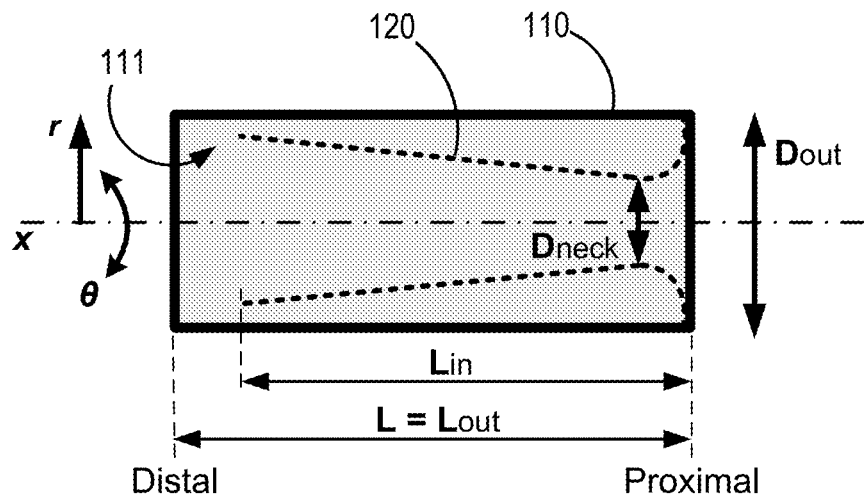
FIG. 3 conceptually illustrates the medical apparatus, according to some embodiments of the invention, and its annotated dimensions.
Figure 7:
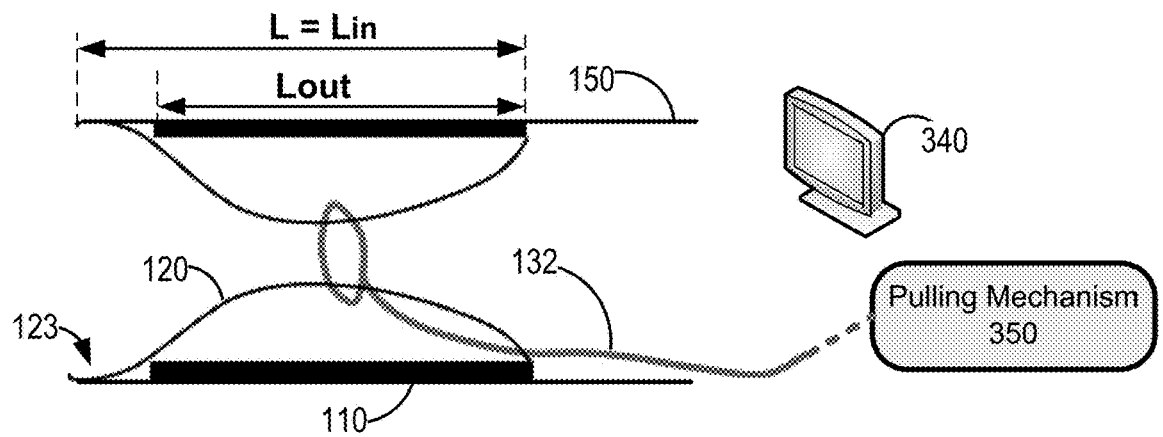
FIG. 7 conceptually illustrates methods of use of the medical apparatus, according to some embodiments of the invention, optionally including a step of monitoring and/or a pulling mechanism for a step of adjusting.

FIG. 3 demonstrates an example where the overall length of the apparatus L is determined by the length of the outer tubular wall ($L=L_{out}$); alternately, FIG. 7 demonstrates an example where the overall length of the apparatus L is determined by the length of the inner tubular wall ($L=L_{in}$). FIG. 7 also demonstrates embodiments where the inner tubular wall extends out of the outer tubular wall ($L_{in}>L_{out}$) and where at least a part of the protruding section (123) of the inner tubular wall (120) is in contact with the anatomical blood vessel (150).

According to some embodiments, the constricting element (130) comprises a loop section (131), which can comprise one of: a ring, a band, a hoop, a noose, a hitch and any combination thereof.

According to some embodiments, the circumference of the loop section (131) is predetermined and fixed before delivery into the anatomical blood vessel. According to some embodiments, the circumference of the loop section (131) can be adjusted. The circumference adjustment can be conducted prior to the insertion of the medical apparatus (100) into the anatomical blood vessel (150). For a non-limiting example, a physician's (or a care giver) prior to insertion adjustment is according to the patient's clinical condition. Alternatively, the circumference adjustment can be conducted while the medical apparatus is within the blood vessel (150), e.g. during the implantation procedure and/or any time after implantation. According to some embodiments the adjustment can be gradual, i.e., over hours, days or weeks after implantation. According to some embodiments, the adjustable loop section (131) can be only tightened, and according to some embodiments it can be expandable as well, for a non-limiting example the adjustable loop section (131) can be expanded by an inflatable balloon (330), as demonstrated in FIG. 8A, and after expansion in FIG. 8B.

Figure 11:
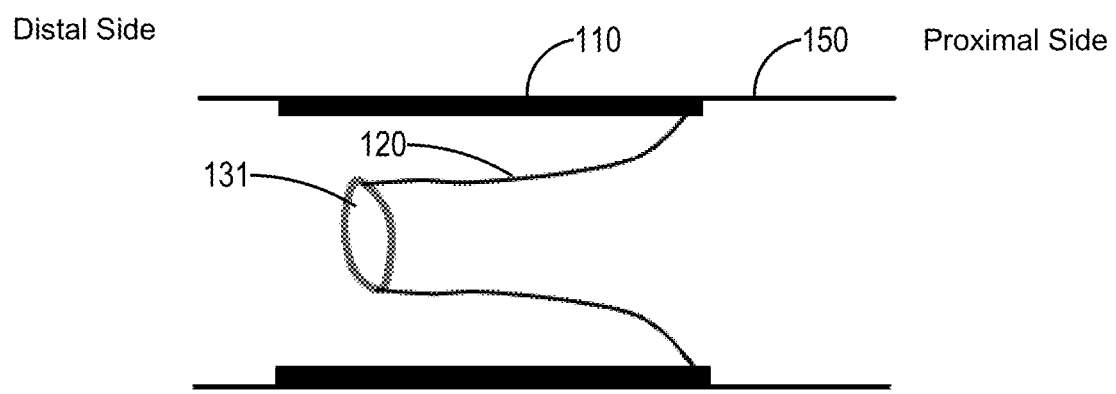
FIG. 11 conceptually illustrates the medical apparatus, according to some embodiments of the invention, where the constricting element is deployed at the distal end of the inner tubular wall.

According to some embodiments, the loop section (131) can be positioned at any location along the longitudinal axis X of the inner tubular wall (120). According to some embodiments, the loop section (131) is deployed at a predetermined location, prior to insertion of the medical apparatus to the blood vessel (150), as demonstrated in FIGS. 6A and 11. FIG. 11 demonstrates fixation of the loop section (131) at the distal end of the inner tubular wall (120), where the medical apparatus (100) is shown after its implantation within the anatomical blood vessel.

Figure 9A:
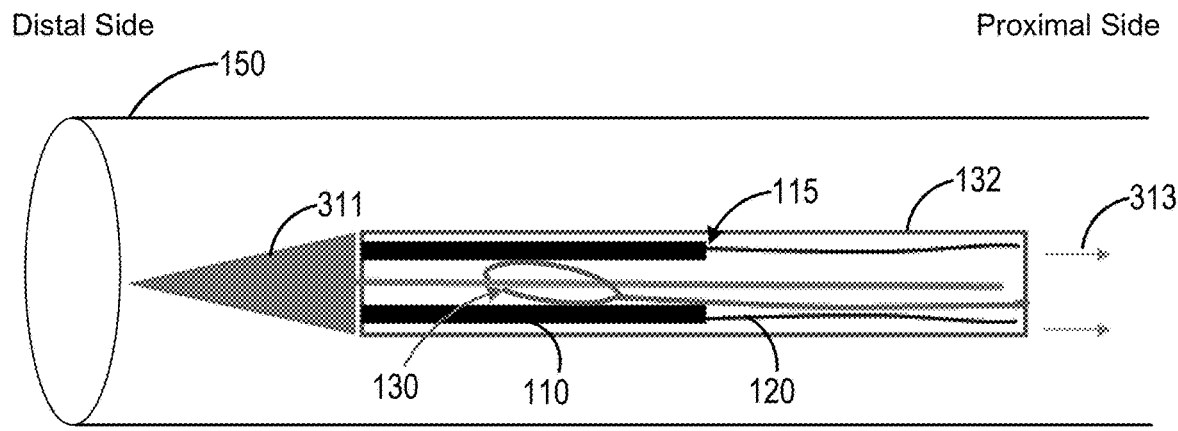
FIGS. 9A, 9B and 9C conceptually illustrate methods of use of the medical apparatus, according to some embodiments of the invention, including a step of delivering (FIG. 9A) the medical apparatus into a blood vessel, as one long tubular wall and a step of forming (FIGS. 9B and 9C) the inner tubular wall, by pushing the proximal end of the outer tubular wall there-into, while the medical apparatus is deployed within the blood vessel.
Figure 9B:
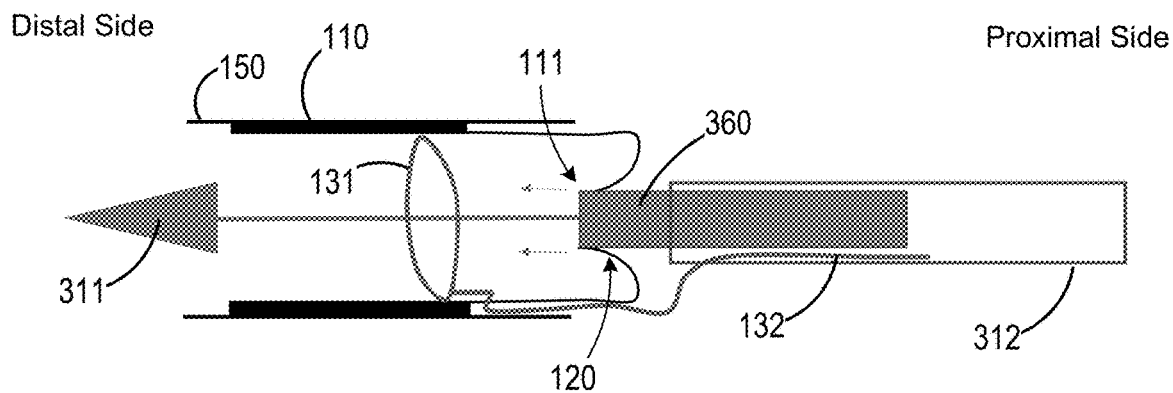
Figure 9C:
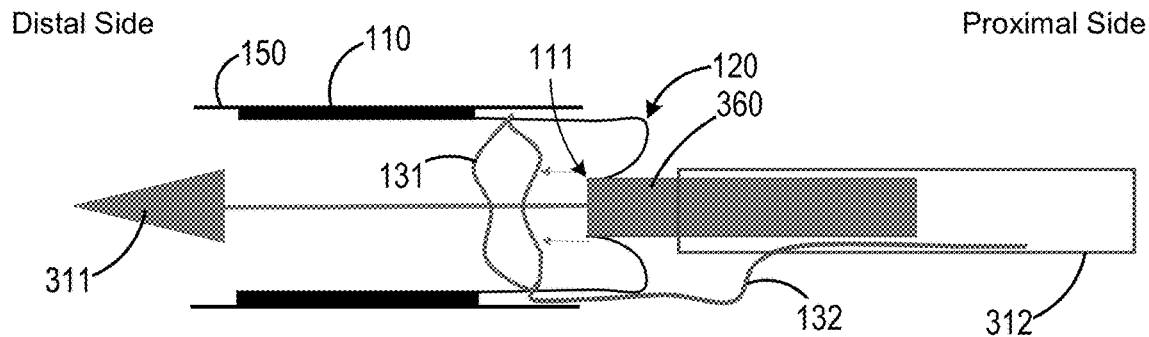
Figure 12:
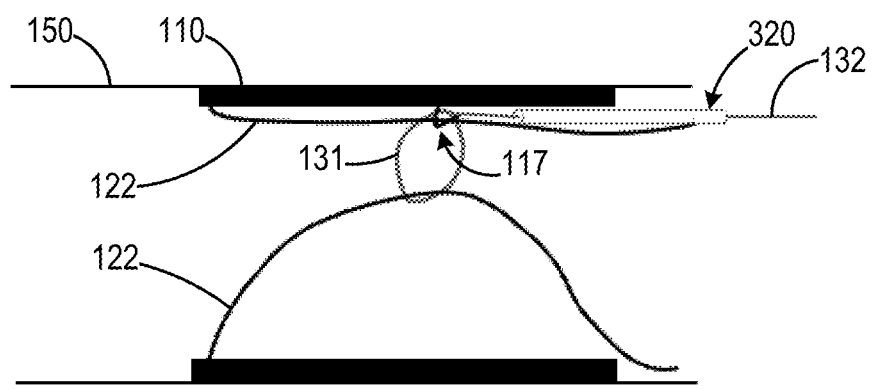
FIG. 12 conceptually illustrates the medical apparatus, according to some embodiments of the invention, where the medical apparatus comprises non-concentric tubular walls.

According to some embodiments, the loop section (131) is fixated at a particular location along the longitudinal axis X by at least partially weaving the loop section (131) through the struts of the outer tubular wall (110), as demonstrated in FIGS. 9C and 12, thereby securing the loop section (131) in place.

Figure 6A:
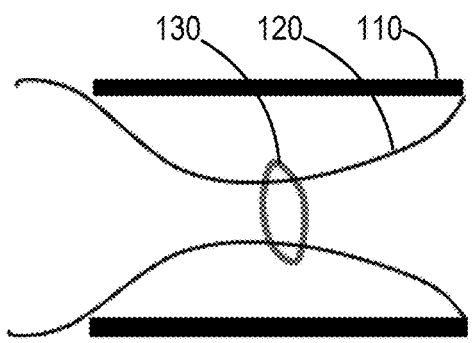
FIGS. 6A, 6B and 6C conceptually illustrate methods of use of the medical apparatus, according to some embodiments of the invention, where
Figure 6B:
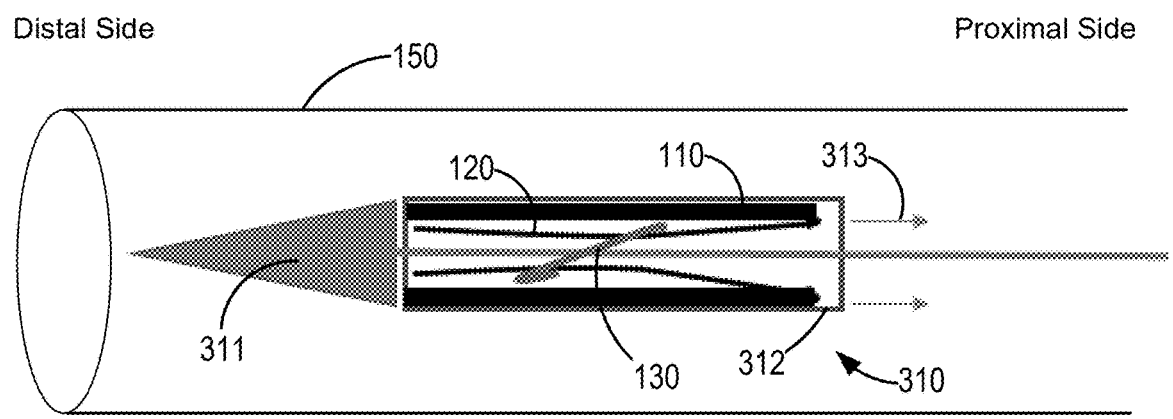

According to some embodiments, the medical apparatus (100) is collapsible and self-expanding and is configured to be delivered into an anatomical blood vessel (150) via a delivering system, e.g. a catheter (310), as demonstrated in FIG. 6B. In this example, the catheter's tip is marked by a large arrow (311) pointing to the direction of its' insertion; the withdrawal direction of the catheter's outer sheath (312), which releases the medical apparatus (100) into the anatomical blood vessel (150), is marked by small arrows (313). According to some embodiments, the medical apparatus (100) can be provided to the physician (or a care giver) together with the delivering catheter (310), where the medical apparatus (100) is already crimped there within, as shown in FIG. 6B.

According to some embodiments, the constricting element (130) further comprises a tail section (132) configured to be pulled (or pushed, if the tail section is non-flexible), in some embodiments, by a mechanism in the handle of the delivery system and thereby adjust the circumference of the loop section (131) and accordingly the neck section (125) of the inner tubular wall.

According to some embodiments, the constricting element comprises an adjusting mechanism (320). In one embodiment, the adjusting mechanism (320) comprises a folded wire, where the folded section is passed through a tube element (321) and forms the loop section (136), which extends out the distal end of the tube element (321), and where two tail sections (132) extend out of the proximal end of the tube element (321). In another embodiment the adjusting mechanism (320) comprises a looped wire with a sliding knot (hence the loop section), with the single wire passed through a tube element (321) and extending out of its distal end, and where the wire's single tail (hence tail section), extends out of the tube element's (321) proximal end. According to both adjusting mechanism (320) examples, by pulling the wire's tail section/s (132), while holding the tube element (321) stationary, the wire's loop section (136) is tightened and thereby its circumference is reduced.

According to some embodiment, the proximal end of the adjusting mechanism (320) can be extended out of the blood vessel and into a subcutaneous space, which can provide access for post procedure adjustment (e.g. post implantation adjustment). More specifically, the wire's tail section/s (132) together with the proximal end of the tube element (321) can be extended out of the blood vessel and into a subcutaneous space.

According to some embodiments, the tail section (132) extends out of the blood vessel, for a non-limiting example, through the right side of the heart and to a subcutaneous space. According to some embodiments, an actuator (350) can further pull and/or push the proximal end of the tail section (132) for adjustment of the circumference of the loop section (131) of the constricting element (130), as demonstrated in FIG. 7.

Figure 6C:
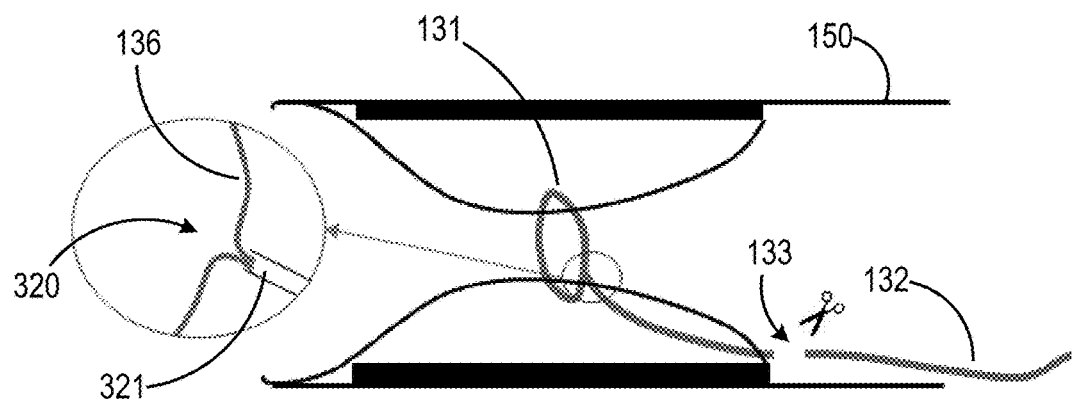

According to some embodiments, the loop section (131), after its circumference adjustment, can be temporarily or permanently fixed or locked to the selected circumference, and according to some embodiments, the tail section (132) can be detached (133) from the loop section (131), for a non-limiting example, at a point near the medical apparatus, as demonstrated in FIG. 6C.

According to some embodiments, the medical apparatus (100) is delivered as a single tubular wall (115) where the inner tubular (120) wall is formed by radially folding at least one end (distal and/or proximal end) of the single tubular wall (115) there-into and into the loop section (130), and thereby to form the inner tubular wall (120) with a diameter $D_{in} < D_{out}$. According to some embodiments, the folding and forming of the inner tubular wall (120) can be conducted at a prior stage, e.g. at the manufacturing stage, as demonstrated in FIGS. 4A and 4B, or while within the anatomical blood vessel (150), as demonstrated in FIGS. 9A-9C.

According to some embodiments the present invention provides a method (200) for reducing the effective diameter of an anatomic vessel (150). The method (200) comprising steps of:
providing (210) a medical apparatus (100) having an inner tubular wall (120) within an outer tubular wall (110);
deploying (220) the medical apparatus within an anatomical blood vessel; and
constricting (230) at least a portion (121) of the inner tubular wall (120), thereby providing the inner tubular wall (120) with a radial neck section (125).

According to some embodiments, the step of constricting (230) is configured for forming a diametrical reducer for the anatomical blood vessel (150). According to some embodiments, the constricting is gradual, by means of step wise constriction over a predetermined period of time, for a non-limiting example, every couple of days or weeks; which can lead to a gradual and controlled reduction of the effective diameter of the anatomical blood vessel.

According to some embodiments, the step of providing (210) further comprises providing (211) the medical apparatus with a constricting element (130) configured for the constricting of the portion (121) of the inner tubular wall (120). According to some embodiments, the constricting element (130) comprises a loop section (131) and can further comprise a tail section (132), as detailed above.

According to some embodiments, the step of constricting (230) further comprises adjusting (231) the constriction. Adjusting the constriction can be at any time of the treatment procedure, i.e. before deployment of the medical apparatus (as in FIG. 6A), during the deployment (while at least part of the delivery system is in the anatomical vessel), and after the step of the deploying (220); according to the latter (after the deployment), the step of adjusting (231) is conducted while the medical apparatus is within the anatomical vessel (150), as demonstrated in FIGS. 6C, 7 and 10.

According to some embodiments, the adjusting can be gradual, for gradual and controlled adjustment of the effective diameter of the anatomical blood vessel.

According to some embodiments, the step of deploying (220) comprises delivering (221) the medical apparatus by a trans-catheter procedure into the anatomical blood vessel (150) via a catheter (310), as demonstrated in FIGS. 6B and 9A.

Figure 8A:
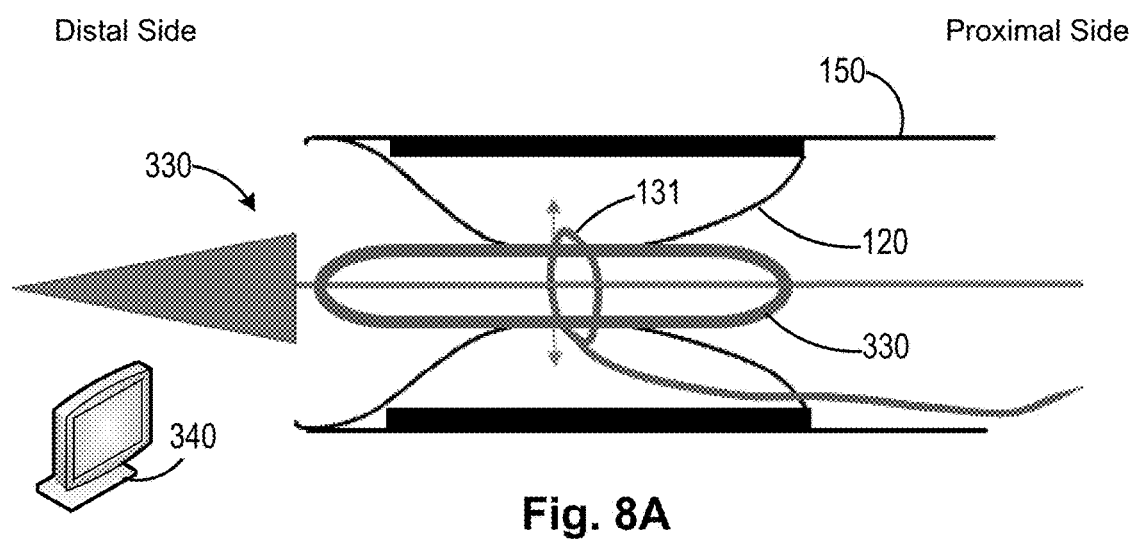
FIGS. 8A and 8B conceptually illustrate methods of use of the medical apparatus, according to some embodiments of the invention, including a step of expanding of the constricted section of the inner tubular wall (FIG. 8A), and after the expansion (FIG. 8B)

According to some embodiments, the method (200) further comprises a step of expanding (240) the constricted portion of the inner tubular wall, while within the anatomical blood vessel (150), for a non-limiting example: by an inflatable balloon (330), delivered and controlled by a catheter (331), as demonstrated in FIG. 8A, or according to another non-limiting example by the adjusting mechanism (320), as described in FIGS. 6C and 12, in the case where the wire is non-flexible. According to some embodiments, the expanding takes place either at the end of the treatment, in which the constriction is expanded to terminate the therapy, or during the deployment process, where the expanding may be required in the case where the medical apparatus has been constricted too tightly, and needs to be expanded and retightened again. According to some embodiments the expanding can be gradual.

According to some embodiments, the method (200) further comprises a step of temporarily or permanently locking (250) the constricted section of the inner tabular wall (120) to a specific circumference. According to some embodiments, the locking can be performed by using a locking mechanism (372) for the constricted area of the inner tubular wall (120), for a non-limiting example as demonstrated in FIG. 14.

According to some embodiments, the method (200) further comprises a step of detaching (260) the tail section (132) of the constricting element (130), according to some embodiments after the step of locking (250), as demonstrated in FIG. 6C (133). The tail section (132) can then be retracted out of the anatomical blood vessel and patient's body together with the delivery system.

According to some embodiments, in the case where the medical apparatus (100) is delivered as a single tubular wall (115), the providing (210) comprises forming (212) the inner tubular wall (120) by pushing in at least one end-portion (111) of the single tubular wall (115) and radially folding thereof into. According to some embodiments, the step of forming (212) can be performed before the step of deploying (220) the medical apparatus; according to other embodiments the step of forming (212) can be performed after the step of deploying (220), while the medical apparatus (100) is within the anatomical blood vessel (150), by using a catheter (360). According to a preferred embodiment, the forming (212), before or while the medical apparatus is within the blood vessel, can be achieved when at least part of the single tubular wall (115) is manufactured by a braiding process.

According to some embodiments, the method (200) further comprises monitoring (270) at least one physiological parameter, in order examine the effects of treatment by use of the medical apparatus. According to some embodiments, the monitoring (270) is performed during at least one of the steps of: deploying (220), delivering (221), forming (212), constricting (230), adjusting (231), expanding (240), locking (250) and detaching (260). According to a preferred embodiment, the monitoring (270) is configured for the adjusting (231) of the constriction of the inner tubular wall (120). According to some embodiments, the at least one monitored physiological parameter can be compared to a baseline reading of the same (e.g. prior to treatment), in order examine the effects of treatment.

According to some embodiments, monitoring (270), comprises at least one of:

measuring blood pressure; for non-limiting examples:
   measuring the right ventricle (RV) systolic pressure, measuring the left ventricle (LV) systolic pressure; measuring the RV diastolic pressure; measuring the LV diastolic pressure; measuring the pressure gradient across the vessel constriction;

imaging the constricted anatomical blood vessel and/or it's adjacent blood vessel/s, and measuring degree of the vessel/s's constriction; and measuring heart rate;

any combination thereof.

According to some embodiments, a therapeutic result for the use of the medical apparatus (100) can be at least one of the group consisting of:

an increase in the left ventricle ejection fraction (LVEF);

a decrease in the left ventricle end diastolic pressure (LVEDP);

improvement in the clinical symptoms of heart failure; and any combination thereof.

Figure 2:
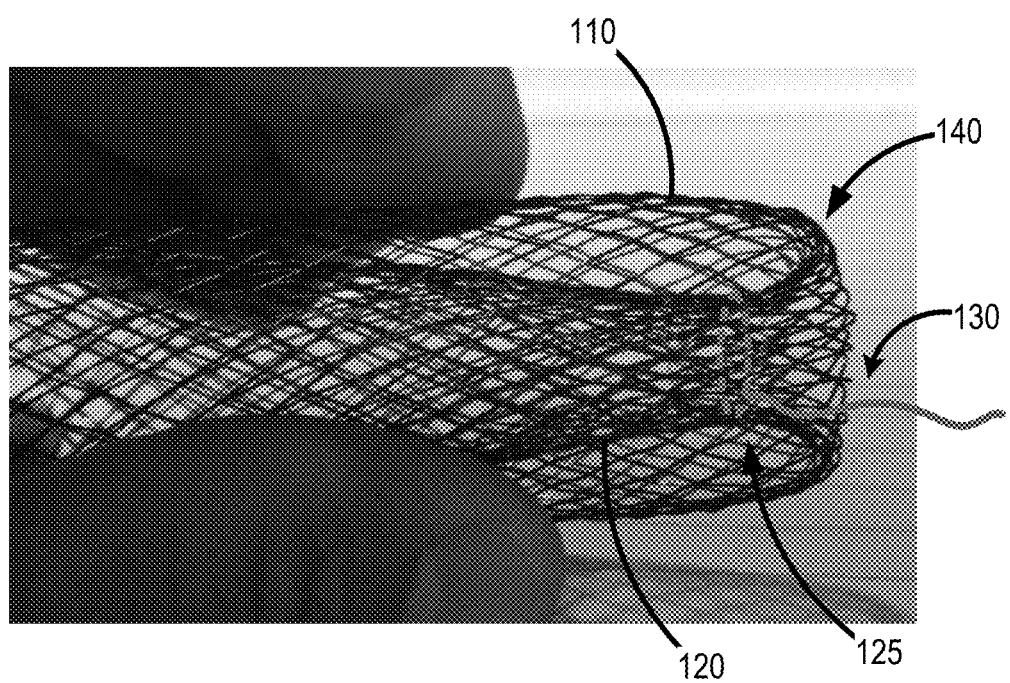
FIG. 2 conceptually depicts the medical apparatus, according to some embodiments of the invention, where a portion of the inner tubular wall is constricted.

Reference is now made to FIGS. 1 and 2 (side views), which conceptually depict the medical apparatus (100), according to some embodiments of the invention, having an outer tubular wall (110), an inner tubular wall (120), and a constricting element (130) comprised of a loop section (131) and a tail section (132). The constricting element (130) is configured to constrict a circumference (121) of a portion of the inner tubular wall (120) and provide the inner tubular wall with a radial neck section (125), as shown in FIGS. 1 and 2, before and after constriction (respectively).

Reference is now made to FIG. 3 (side cross-sectional view), which conceptually illustrates the medical apparatus, according to some embodiments of the invention, and its annotated dimensions. FIG. 3 shows: the medical apparatus's longitudinal axis X, radial axis r and angular axis θ, according to a cylindrical coordinate system; the outer diameter of the medical apparatus (100), which is actually the diameter of the outer tubular wall $D_{out}$, the diameter at the narrowest section of the inner tubular wall $D_{neck}$; the longitudinal length of the inner tubular wall $L_{in}$; and the total length of the medical apparatus L, which in this case is the length of the outer tubular wall.

Figure 4A:
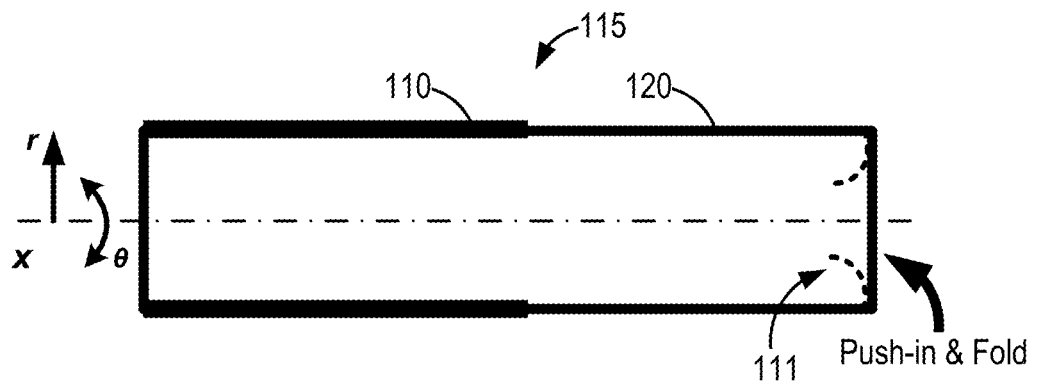
FIGS. 4A and 4B conceptually illustrate and depict the formation of the inner tubular wall, according to some embodiments of the invention.
Figure 4B:
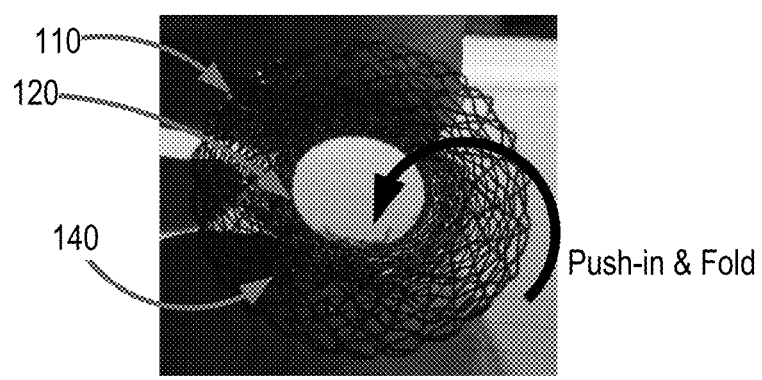

Reference is now made to FIGS. 4A and 4B (side cross-sectional view and front view, respectively), which conceptually illustrate and depict the formation of the inner tubular wall, according to some embodiments of the invention. According to some embodiments, the medical apparatus (100) is manufactured as a single tubular wall (115). The inner tubular (120) wall is formed by radially folding at least one end (distal and/or proximal) of the single tubular wall (115) there-into and according to some embodiments also into the loop section, and thereby forming the inner tubular wall (120) with a diameter $D_{in}<D_{out}$.

FIGS. 4A and 4B demonstrate the folding and forming of the inner tubular wall (120) conducted at a prior stage, e.g. at the manufacturing stage. FIG. 4A demonstrates a longitudinal view at the beginning of the folding process, while FIG. 4B depicts a frontal view, demonstrating the folded arched section (140). FIGS. 9A-9C demonstrate the folding and forming of the inner tubular wall (120) conducted while the medical apparatus is within the anatomical blood vessel (150).

According to a preferred embodiment, the forming, before or while the medical apparatus is within the blood vessel, can be achieved when at least part of the single tubular wall (115) is manufactured by a braiding process.

Reference is now made to FIG. 5 (side view), which conceptually depicts the medical apparatus (100), according to some embodiments of the invention, where the outer tubular wall (110) is manufactured by laser cut process (119), and the inner tubular wall (120) is manufactured by braiding process (129). FIG. 5 further demonstrates the inner tubular wall (120) coated with a coating material (128) configured to cause the blood flowing through the blood vessel to primarily flow through the constricted section of the inner tubular wall. FIG. 5 further demonstrates that the inner and outer tubular walls (110,120) are connected at their distal end (127) by suture connection or by any other means known in the art.

Reference is now made to FIGS. 6A, 6B and 6C (side cross section views), which conceptually illustrate methods of use of the medical apparatus, according to some embodiments of the invention. FIG. 6A illustrates a step of providing of the medical apparatus, where the circumference of the constricting element (130) is set or adjusted at a prior stage, e.g. at the time of manufacture and/or before the deployment of the medical apparatus (100) within the blood vessel.

FIG. 6B illustrates a step of delivering into the blood vessel, where the medical apparatus is in a collapsed configuration, being delivered be a catheter (310). The catheter's tip is marked by a large arrow (311) which points to the direction of its' insertion, and the small arrows point to the withdrawal direction of the catheter's sheath (312), which releases the medical apparatus (100) into the anatomical blood vessel (150).

FIG. 6C illustrates a step of adjusting of the constricting element (130). According to some embodiments the at least a portion (121) of the inner tubular wall (120) is tightened and adjusted by an adjusting mechanism (320). According to some embodiments the adjusting mechanism (320) comprises a folded wire which is at least partially passed through a tube element (321). The wire is therefore configured to have the loop section (136) which extends out the distal end of tube element (321) and two tail wires, as the tail section (132), which extend out of the proximal end of the tube element (321). According to some embodiments, the adjusting mechanism (320) comprises a looped wire with a sliding knot with the single wire passed through a tube element (321). The wire is therefore configured to have the loop section (136) which extends out the distal end of tube element (321) and the tail section (132) which extends out of the proximal end of the tube element (321).

A counter-force holding the tube element (321) stationary, while the wire tails (132) is/are pulled or pushed, can tighten or expand the circumference of the wire loop section (136), respectively.

According to some embodiments, the tube element and the wire tail section extend out of the blood vessels and to a subcutaneous space for access for later adjustment. According to other embodiments the tube and the wire tail are connected to, and operated by, the delivery system.

FIG. 6C further demonstrates the optional step of detaching (260) at least a part of the tail section from the constricting element (133); the tail section (132) can then be retracted out of the anatomical blood vessel and out of the patient's body.

Reference is now made to FIG. 7 (side cross section view), which conceptually illustrates methods of use of the medical apparatus, according to some embodiments of the invention. FIG. 7 demonstrates the step of monitoring (260), as mentioned above, optionally using a monitoring device (340) for displaying the monitoring features. FIG. 7 further demonstrates an actuator or a pulling mechanism (350)

connected to the tail section (132) of the constricting element (130), configured for the step of adjusting (231), where the tail section (132) is pulled by a mechanism in the handle (not shown) of the delivery system, or where the tail section extends out of the blood vessel and to a position in the subcutaneous space, where it can be later used to adjust the level of constriction.

Figure 8B:
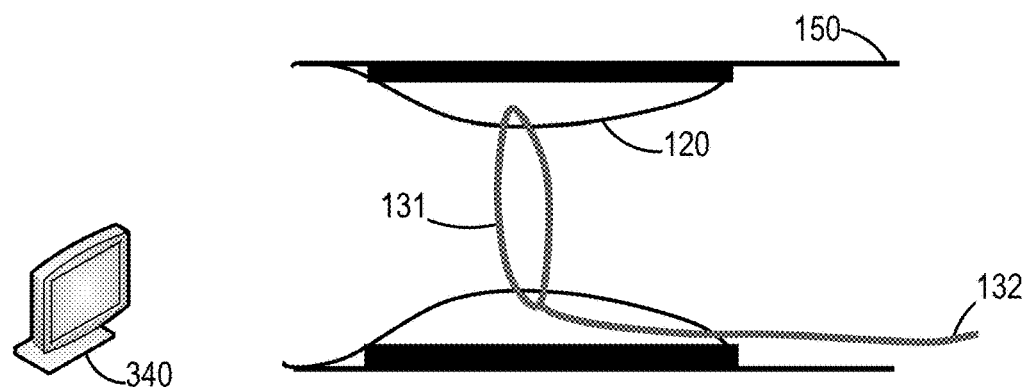

Reference is now made to FIGS. 8A and 8B (side cross section views), which conceptually illustrate methods use of the medical apparatus, according to some embodiments of the invention. FIG. 8A demonstrates the step of expanding (240) of the constricted section together with the loop section (131), using an inflatable balloon (330) being delivered and controlled be a catheter (331). FIG. 8B demonstrates the constricted section after the expansion. As mentioned above, the steps of adjusting, expanding and detaching can be monitored and displayed by the monitoring device (340).

Reference is now made to FIGS. 9A, 9B and 9C (side cross section views), which conceptually illustrate the formation of the inner tubular wall (120), while the medical apparatus is within the anatomical blood vessel (150), according to some embodiments of the invention. FIG. 9A demonstrates the step of delivering the medical apparatus into a blood vessel (150), as a collapsed long single tubular wall (115), delivered by catheter (310).

FIGS. 9B and 9C demonstrate the step of forming (212) the inner tubular wall (120), by pushing the proximal end (111) of the long tubular wall (115) and radially folding it there-into. According to a non-limiting example of FIG. 9B, the loop section (131) can be pre-positioned within the single tubular wall (115) close to the inner circumference of what will later be the outer tubular wall (but not attached to it), and after the folding step, the loop section (131) is positioned between the outer (110) and the inner (120) tubular walls.

According to a non-limiting example of FIG. 9C, the loop section (131) can be initially attached (for example braided) to the single tubular wall (115) along the outer circumference of what will later be the inner tubular wall, and then be radially folded together with the proximal end (111); therefore after the folding step, the loop section (131) remains along the outer circumference of the newly formed inner tubular wall (120).

The forming is conducted by the delivery system (310) having a tubular pushing tube (360).

Figure 10:
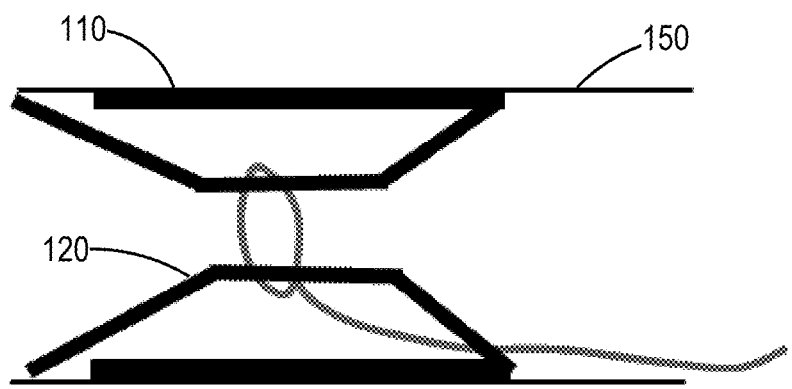
FIG. 10 conceptually illustrates the medical apparatus, according to some embodiments of the invention, where both the outer and the inner tubular walls are manufactured by laser cut process.

Reference is now made to FIG. 10 (side cross section view), which conceptually illustrates the medical apparatus, according to some embodiments of the invention, where both the outer (110) and the inner (120) tubular walls are manufactured by laser cut process, and therefore both are configured with a firm construction.

Reference is now made to FIG. 11 (side cross section view), which conceptually illustrates the medical apparatus, according to some embodiments of the invention, where the constricting element (130) is positioned at the distal end of the inner tubular wall, and thereby providing the medical apparatus with a nozzle configuration.

Reference is now made to FIG. 12 (side cross section view), which conceptually illustrates the medical apparatus, according to some embodiments of the invention, where the medical apparatus (100) comprises non-concentric tubular walls (110,122). FIG. 12 describes a non-limiting example where the loop section (131) is connected or anchored to the inner surface of the outer tubular wall (110) at least at one circumferential location (117) which anchors the loop section (131) and prevents it from moving in a longitudinal direction, or dislodging from the medical apparatus. According to the presented example of FIG. 12, the anchored loop section (131) is further prevented from radial migration of the connection location (117), and therefore the constricted inner tubular wall (120) is pulled towards the anchoring location (117). By pulling on the tail section (132), the loop section (131) tightens the inner tubular wall (122) into a constricted diameter that is not concentric with the outer tubular wall (110). FIG. 12 further demonstrates the configuration of the constricting element configured as the adjusting mechanism (320) having a wire and a tube element.

Figure 13:
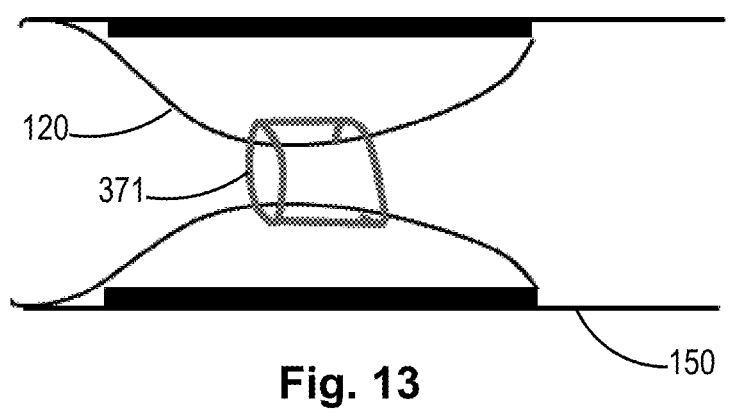
FIG. 13 conceptually illustrates the medical apparatus, according to some embodiments of the invention, where the constricting element comprises a wide band.

Reference is now made to FIG. 13 (side cross section view), which conceptually illustrates the medical apparatus, according to some embodiments of the invention, where the constricting element comprises a wide band (371), configured for a longer section of constricted diameter, which in some embodiments provides a more stable flow pattern and/or a more pronounce pressure differential across the medical apparatus during blood flow.

Figure 14:
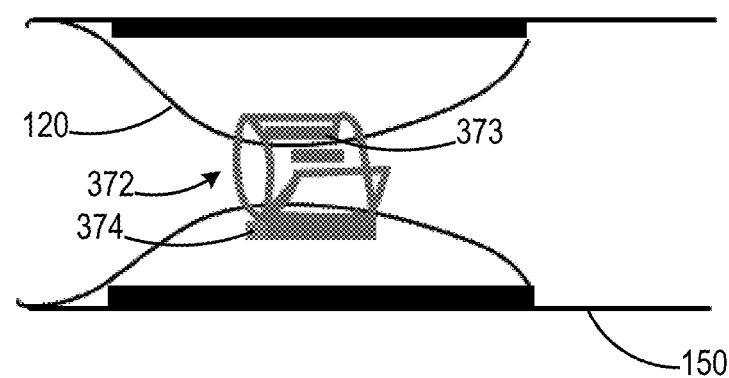
FIG. 14 conceptually illustrates the medical apparatus, according to some embodiments of the invention, further comprising a locking mechanism for the constricted section of the inner tubular wall.

Reference is now made to FIG. 14 (side cross section view), which conceptually illustrates the medical apparatus, according to some embodiments of the invention, further comprising a locking mechanism (372) for the constricted section of the inner tubular wall (120). According to some embodiment, the locking mechanism (372) comprises a band with ratchet pins (373) and a screw connection (374), such that the band can be can be tightened by tightening the screw connection, and remain fixed at the set tightened position. According to some embodiments the screw is operated by a mechanism in the delivery system.

Figures 15A, 15B:
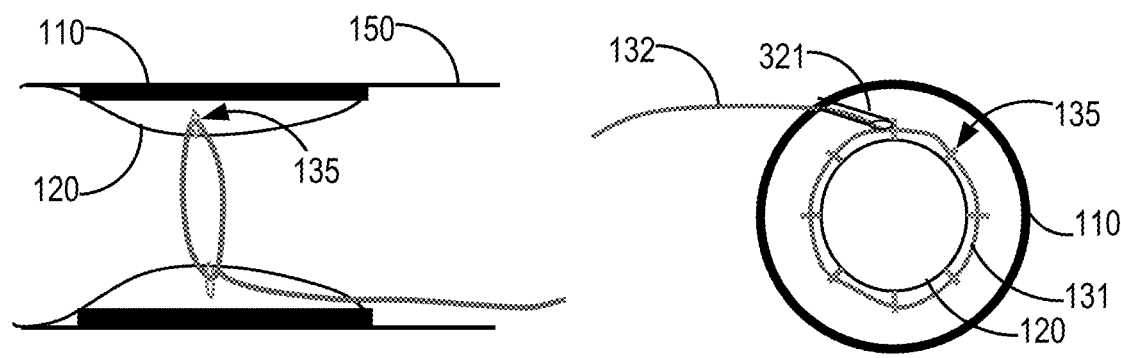
FIGS. 15A and 15B conceptually illustrate the medical apparatus, according to some embodiments of the invention (front and side views respectively), where the constriction element further comprises at least one fixation element.

Reference is now made to FIGS. 15A and 15B (side cross section view and front cross section view, respectively), which conceptually illustrate the medical apparatus, according to some embodiments of the invention, where the constriction element (130) further comprises at least one fixation element (135), which in this example is located on the exterior circumference of the inner tubular wall. The at least one fixation element (135) is configured to specifically position the loop section (131) of the constriction element and prevent it from longitudinal movement, while allowing its degree of constriction to be adjusted. According so some embodiments, the fixation element/s (135) comprise at least one of: a ring, a band, a suture, a hook, a hoop, a noose, a hitch and any combination thereof.

Figure 16:
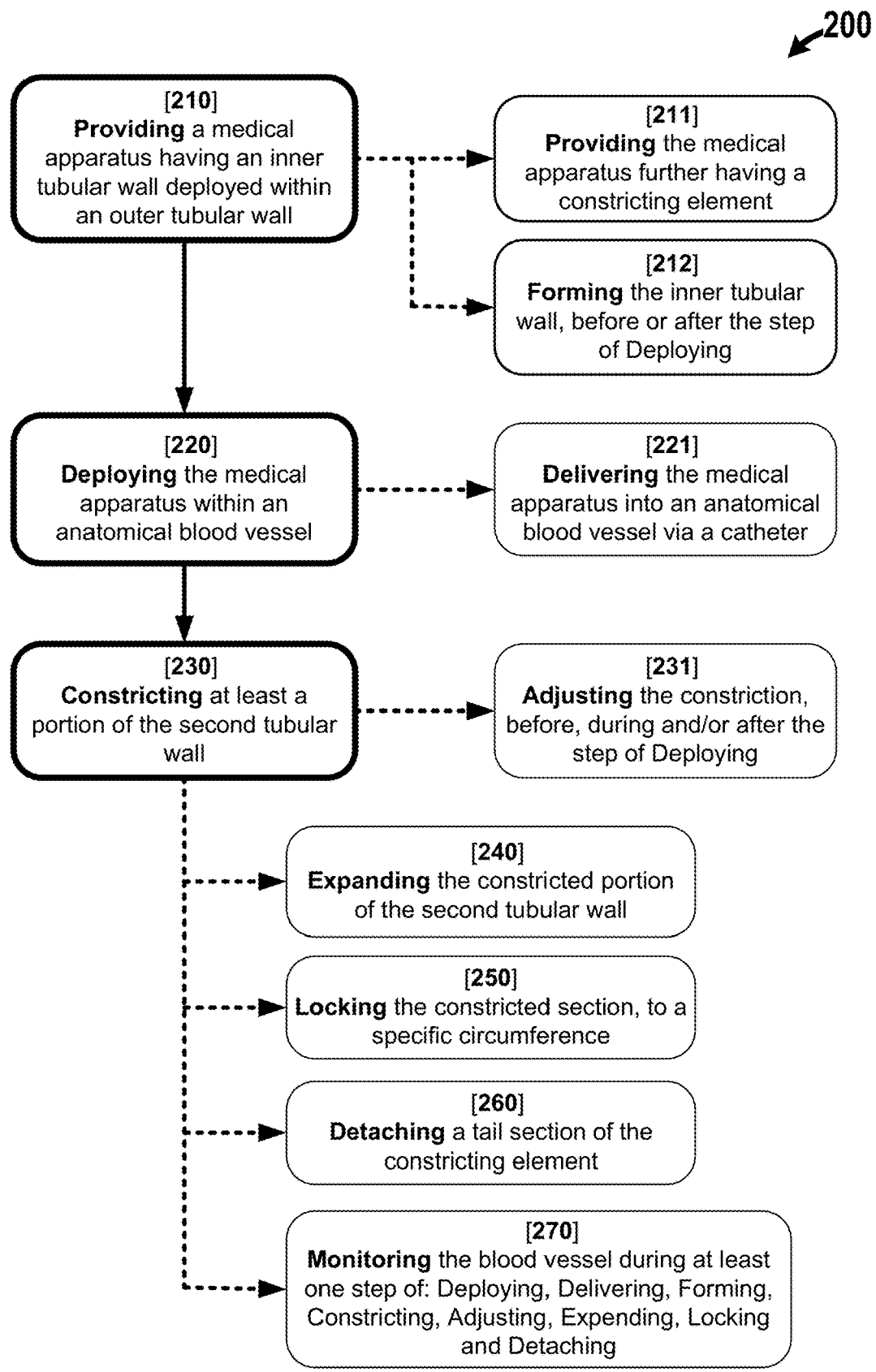
FIG. 16 conceptually illustrates method of use steps for the medical apparatus, according to some embodiments of the invention.

Reference is now made to FIG. 16, which conceptually illustrates optional method of use steps for the medical apparatus, according to some embodiments of the invention. FIG. 16 shows the method steps in a map-like configuration, to conceptually demonstrate the optional method paths.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A medical apparatus comprising:
   a first tubular wall, sized for deployment within a blood vessel;
   a second tubular wall, within the first tubular wall, and
   a narrow constricting element, at least partially surrounding a portion of the second tubular wall, holding said portion of said second tubular wall to a fixed open circumference, and configured to fixedly hold said portion of said second tubular wall away from said first tubular wall, to form a diametrical reducer, wherein an end of the second tubular wall is connected to an end of the first tubular wall, and wherein the other end of the second tubular wall is not connected to the other end of the first tubular wall to allow a change in the overall longitudinal length of the second tubular wall.

2. The medical apparatus of claim 1, comprising a connector, wherein an end of the second tubular wall is connected to an end of the first tubular wall with the connector, and the diameter of at least one end of the second tubular wall is of the same diameter as the first tubular wall, at least at one end.

3. The medical apparatus of claim 1, wherein at least a portion of the second tubular wall is coated with a coating material.

4. The medical apparatus of claim 1, wherein at least one of the following holds true:
the first and second tubular walls are concentric;
material of the first and second tubular walls comprises at least one of the group consisting of: Nitinol, stainless steel, Titanium, Cobalt-Chromium alloy, Tantalum alloy, polymer, Platinum alloy and any combination thereof;
the first tubular wall is made of a first material and the second tubular wall is made of a second material.

5. The medical apparatus of claim 1, wherein the first and second tubular walls are manufactured by a process selected from: laser cutting, braiding, any combination thereof.

6. The medical apparatus of claim 1, wherein the ratio between the medical apparatus's longitudinal length (L) and diameter of the first tubular wall (Dout) is smaller than 2.

7. The medical apparatus of claim 1, wherein the constricting element comprises a loop section.

8. The medical apparatus of claim 7, wherein the constricting element comprises a tail section configured to be pulled and/or pushed to adjust a circumference of the loop section.

9. The medical apparatus of claim 8, comprising a locking mechanism that is configured to lock the circumference of the loop section at an adjusted circumference.

10. The medical apparatus of claim 9, wherein the tail is configured to be detached after adjustment of the loop section circumference.

11. The medical apparatus of claim 1, wherein the constricting element is configured for circumference adjustment of the second tubular wall, while the medical apparatus is within the anatomic vessel.

12. The medical apparatus of claim 1, wherein the medical apparatus is collapsible and configured to be delivered into the anatomic vessel via a catheter.

13. The medical apparatus according to claim 1 comprising a fixation element configured to fixate the constricting element.

14. The medical apparatus of claim 13, wherein the constricting element is a loop element and the fixation element is at least one of a ring, a band, a suture, a hook, a hoop, a noose, and a hitch.

15. The medical apparatus of claim 1, wherein the constricting element constricts the circumference of the portion of the second tubular wall without constricting a circumference of the first tubular wall.

16. The medical apparatus of claim 1, wherein said portion of said second tubular wall is located at a central region of said second tubular wall.

17. The medical apparatus of claim 1, wherein said first tubular wall and said second tubular wall are separately formed and then attached at their ends.

18. The medical apparatus of claim 1, wherein said narrow constricting element is mounted on said second tubular wall and not attached to said first tubular wall.

19. The medical apparatus of claim 1, wherein said portion has a cross-section, at an axially narrow section thereof, smaller than a both a distally adjacent portion and a proximally adjacent portion.

20. The medical apparatus of claim 1, wherein said narrow constricting element is elongate and extends in a direction at least partially surrounding said portion.

21. The medical apparatus of claim 1, wherein said narrow constricting element circumferentially surrounds said portion.

22. The medical apparatus of claim 1, wherein said tubular walls are sized and shaped for anchoring in a main or branch pulmonary artery and said constricting element fixedly constricts said second tubular element to effectively reduce arterial diameter.

23. The medical apparatus of claim 1 wherein said narrow constricting element forms the short and narrow radial neck on said second tubular wall with the steep reduction of the diameter.

24. The medical apparatus of claim 1 wherein the diameter at least at one end of the second tubular wall uniformly reduces toward the short and narrow radial neck.

25. The medical apparatus of claim 24 wherein the blood vessel is a pulmonary artery of an adult.

26. The medical apparatus of claim 1 wherein the blood vessel is a pulmonary artery.

27. The medical apparatus of claim 1 wherein the first tubular wall and the second tubular wall are manufactured to form a single unit by the connection thereof.

28. The medical apparatus of claim 27, wherein an end of the second tubular wall is axially aligned with an end of the first tubular wall, and wherein said end of the second tubular wall and said end of the first tubular wall are of the same diameter.

29. A method for reduction of effective diameter of an anatomic vessel comprising:
providing a medical apparatus comprising a second tubular wall within a first tubular wall and a narrow constricting element at least partially surrounding a portion of the second tubular, fixedly holding said second tubular wall to a fixed open circumference, and holding said portion of said second tubular wall away from said first tubular wall, wherein the first tubular wall and the second tubular wall are manufactured as a single unit;
deploying the medical apparatus as a single unit within an anatomical blood vessel, wherein said blood vessel comprises a pulmonary artery.

30. The method of claim 29, comprising constricting at least a portion of the second tubular wall with said constricting element while the medical apparatus is in the anatomical blood vessel.

31. The method of claim 29, wherein said constricting further comprises adjusting the constriction, before, during, and/or after said deploying.

32. The method of claim 29, wherein said deploying comprises delivering the medical apparatus into the anatomical blood vessel via a catheter and expanding a constricted portion of the second tubular wall, while within the anatomical blood vessel.

33. The method of claim 29, further comprising temporarily or permanently maintaining a constricted portion of the second tubular wall to a specific circumference.

34. The method of claim 29, wherein the at least the portion of the second tubular wall is constricted without constricting a circumference of the first tubular wall.

35. The method of claim 29, wherein the first tubular wall and the second tubular wall are manufactured from a single tubular wall, wherein the second tubular member is formed by radially folding at least one end of the single tubular wall.

36. A medical apparatus comprising:
- a first tubular wall sized for deployment within a blood vessel and having a first tubular wall proximal side and a first tubular wall distal side;
- a second tubular wall, within the first tubular wall having a second tubular wall proximal side and a second tubular wall distal side;
- wherein said first tubular wall and said second tubular wall are connected with said first tubular wall proximal side to said second tubular wall proximal side and said first tubular wall distal side to said second tubular wall distal side;
- wherein said first tubular wall and said second tubular wall are manufactured as a single unit and deployed the first tubular wall and the second tubular wall as a single unit within an anatomical blood vessel;
- wherein said medical apparatus comprises a narrow constricting element coupled to said second tubular wall and configured to fixedly hold a portion of said second tubular wall away from said first tubular wall to form a diametrical reducer to said blood vessel.

37. The medical apparatus of claim 36, wherein said constricting element holds said portion of said second tubular wall to a fixed open circumference.

38. The medical apparatus of claim 37, wherein said portion of said second tubular wall is located at a central region of said second tubular wall.

39. The medical apparatus of claim 36, wherein at least a portion of the second tubular wall is coated with a coating material.

40. The medical apparatus of claim 36, wherein said first tubular wall and said second tubular wall are separately formed and then attached.

41. The medical apparatus of claim 36, wherein the first tubular wall and the second tubular wall are manufactured from a single tubular wall, wherein the second tubular member is formed by radially folding at least one end of the single tubular wall.

* * * * *